United States Patent
Mazumder et al.

(10) Patent No.: US 12,390,145 B2
(45) Date of Patent: Aug. 19, 2025

(54) PERSONALIZED NEUROMOTOR REHABILITATION THERAPY FOR UPPER LIMB USING A NEUROMUSCULOSKELETAL ARM MODEL

(71) Applicant: Tata Consultancy Services Limited, Mumbai (IN)

(72) Inventors: Oishee Mazumder, Kolkata (IN); Aniruddha Sinha, Kolkata (IN); Ayush Rai, Muzaffarpur (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1070 days.

(21) Appl. No.: 17/376,323

(22) Filed: Jul. 15, 2021

(65) Prior Publication Data

US 2022/0054073 A1 Feb. 24, 2022

(30) Foreign Application Priority Data

Jul. 16, 2020 (IN) .............................. 202021030392

(51) Int. Cl.
*G06F 7/48* (2006.01)
*A61B 5/00* (2006.01)
(Continued)

(52) U.S. Cl.
CPC .............. *A61B 5/397* (2021.01); *A61B 5/313* (2021.01); *A61B 5/4836* (2013.01);
(Continued)

(58) Field of Classification Search
CPC ....... A61B 5/397; A61B 5/313; A61B 5/4836; A61B 2505/09; B25J 9/1605;
(Continued)

(56) References Cited

U.S. PATENT DOCUMENTS

| | | | |
|---|---|---|---|
| 9,811,074 B1 * | 11/2017 | Aichele | B25J 9/1656 |
| 10,409,928 B1 * | 9/2019 | De Sapio | G06F 30/20 |
| 2019/0172585 A1 * | 6/2019 | Mazumder | G16H 50/30 |

OTHER PUBLICATIONS

Zhibin Song et al., "A Muscle-Specific Rehabilitation Training Method Based on Muscle Activation and the Optimal Load Orientation Concept," Applied Bionics and Biomechanics, Nov. 2018, vol. 2018 (4), pp. 1-13, Hidawi, https://downloads.hindawi.com/journals/abb/2018/2365983.pdf.

(Continued)

*Primary Examiner* — Nithya J. Moll
(74) *Attorney, Agent, or Firm* — Finnegan, Henderson, Farabow, Garrett & Dunner, LLP

(57) ABSTRACT

This disclosure relates generally to a method and system that provides personalized neuro motor rehabilitation therapy using a musculoskeletal arm model. The arm model is personalized using anthropometric measures and further adapted to operate using an optimized set of muscle actuators considering associated redundancy. The method generates trajectories associated with reach motion profiles for each motion task utilizing joint kinematics and inverse dynamics by integrating forward dynamics and muscle synergy concepts to select the optimized set of muscle actuators. The generated trajectories are further ranked based on muscle synergy, minimum energy consumption and optimized trajectory to select rehabilitation therapy best suited for effective recovery. Conventional methods that work with neural dynamics in deriving muscle synergy are dependent on single tasks, leaving synergy variation with task variability unexplored. The present disclosure provides (Continued)

understanding of work space, task variability and synergy paradigm to derive conclusive control actions for aiding rehabilitation effectively.

20 Claims, 16 Drawing Sheets

(51) Int. Cl.
  *A61B 5/313*  (2021.01)
  *A61B 5/397*  (2021.01)
  *B25J 9/16*  (2006.01)
  *G16H 20/30*  (2018.01)

(52) U.S. Cl.
  CPC ............ *B25J 9/1605* (2013.01); *G16H 20/30* (2018.01); *A61B 2505/09* (2013.01)

(58) Field of Classification Search
  CPC .................. B25J 9/1671; G16H 20/30; G05B 2219/40324; G05B 17/00
  See application file for complete search history.

(56) References Cited

OTHER PUBLICATIONS

Reza Sharif Razavian et al., "A model-based approach to predict muscle synergies using optimization: application to feedback control," Front Comput Neurosci., Oct. 2015, NCBI, https://www.readcube.com/articles/10.3389/fncom.2015.00121.

Mojtaba Sharifi et al., "Nonlinear Optimal Control of Planar Musculoskeletal Arm model with Minimum Muscles Stress Criterion," Journal of Computational and Nonlinear Dynamics, Jan. 2017, vol. 12, Issue: 1, ASME, https://www.researchgate.net/publication/306295769_Nonlinear_Optimal_Control_of_Planar_Musculoskeletal_Arm_Model_With_Minimum_Muscles_Stress_Criterion/link/59bf56620f7e9b48a2989d79/download.

Akbar Nikzad Goltapeh et al., Development a planar neuro-musculoskeletal arm model in post-stroke patients, 26th National and 4th International Iranian Conference on Biomedical Engineering (ICBME), Nov. 2019, IEEE, https://www.researchgate.net/publication/337199946_Development_a_planar_neuro-musculoskeletal_arm_model_in_post-stroke_patients/link/5e4c8fb392851c7f7f456c21/download.

* cited by examiner

Similarity Plot

Synergy for original recruitment

Synergy for similarity value 85% ; Synergy value:8

Synergy for similarity value 75% ; Synergy value:4

Similarity Plot

Synergy for original recruitment

Synergy for similarity value 85% ; Synergy value:8

Synergy for similarity value 75% ; Synergy value: 5

Similarity Plot

Synergy for original recruitment

Synergy for similarity value 85% ; Synergy value: 8

Synergy for similarity value 75% ; Synergy value: 3

PERSONALIZED NEUROMOTOR REHABILITATION THERAPY FOR UPPER LIMB USING A NEUROMUSCULOSKELETAL ARM MODEL

PRIORITY CLAIM

This U.S. patent application claims priority under 35 U.S.C. § 119 to: Indian Patent Application number 202021030392, filed on 16 Jul. 2020. The entire contents of the aforementioned application are incorporated herein by reference.

TECHNICAL FIELD

The disclosure herein generally relates to the field of neuromotor rehabilitation therapy, and, more particularly, to a personalized neuromotor rehabilitation therapy for upper limb using a neuromusculoskeletal arm model.

BACKGROUND

Human musculoskeletal system is highly redundant, creating many ways of muscle recruitment for performing any specific task. This redundancy poses a computational challenge to Central Nervous system (CNS), which in association with sensory and musculoskeletal system tries to simplify control of tasks by mapping initial states and goals into muscle activation through the combination of coordinated recruitment of groups of muscles with specific activation. Recently, there have been numerous studies on reaching toward a point target in human motor control.

Controlling the movement of the arm for point to point motion like reaching for an object is challenging as it requires coordinating numerous muscles acting on many joints and for such tasks, CNS actively recruits muscle synergy to find an optimal trajectory or torque profile. The discrepancy between kinetic-kinematic variables and complexity of muscle pattern underlines the requirement for better understanding of the muscle control mechanism during reaching tasks and correlate synergy variation dependencies on work-space configuration. Several state of art methods exists on synergy control mechanism in post stroke rehabilitation during hand reaching task execution. However, in the prior methods, reaching task synergy calculation is mostly computed on a single task, which are not able to derive conclusive control actions to aid in rehabilitation.

SUMMARY

Embodiments of the present disclosure present technological improvements as solutions to one or more of the above-mentioned technical problems recognized by the inventors in conventional systems.

In an aspect, there is provided a processor implemented method comprising the steps of: personalizing, via one or more hardware processors, a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF; and optimizing, via the one or more hardware processors, the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration: calculating a muscle torque $\tau_m$ indicative of a muscle force based on a moment arm $\lfloor R(q) \rfloor$ wherein q represent a joint angle, an activation value a obtained from a muscle Electromyography (EMG) data, a normalized length l and a normalized velocity $\dot{l}$ of each muscle actuator in the set of muscle actuators; calculating a joint torque indicative of loading on each of the three joints, wherein the joint torque is based on an acceleration $\ddot{q}$ due to the joint torque t, the joint angle q, an inertia tensor function Q, a mass matrix M, a Coriolis component C, a gravity component G and an external force F applied to the neuromusculoskeletal arm model; generating a trajectory associated with a corresponding motion profile for each of the one or more motion tasks based on forward dynamics using the calculated muscle torque and the calculated joint torque; and evaluating a mean square error between the generated trajectory and a target trajectory associated with a corresponding motion profile for each of the one or more motion tasks; until the evaluated mean square error is less than a pre-defined threshold; and identifying, via the one or more hardware processors, the set of the muscle actuators with the reduced number of muscle actuators at the end of the iterative steps as the optimized set of muscle actuators to perform the one or more motion tasks.

In another aspect, there is provided a system comprising: one or more data storage devices operatively coupled to one or more hardware processors via the one or more input/output interfaces and configured to store instructions configured for execution via the one or more hardware processors to: personalize a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF; optimize the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration by: calculating a muscle torque $\tau_m$ indicative of a muscle force based on a moment arm $\lfloor R(q) \rfloor$, wherein q represent a joint angle, an activation value a obtained from a muscle Electromyography (EMG) data, a normalized length l and a normalized velocity $\dot{l}$ of each muscle actuator in the set of muscle actuators; calculating a joint torque indicative of loading on each of the three joints, wherein the joint torque is based on an acceleration $\ddot{q}$ due to the joint torque t, the joint angle q, an inertia tensor function Q, a mass matrix M, a Coriolis component C, a gravity component G and an external force F applied to the neuromusculoskeletal arm model; generating a trajectory associated with a corresponding motion profile for each of the one or more motion tasks based on forward dynamics using the calculated muscle torque and the calculated joint torque; and evaluating a mean square error between the generated trajectory and a target trajectory associated with a corresponding motion profile for each of the one or more motion tasks; until the evaluated mean square error is less than a pre-defined threshold; and identify the set of the muscle actuators with the reduced number of muscle actuators at the end of the iterative steps as the optimized set of muscle actuators to perform the one or more motion tasks.

In yet another aspect, there is provided a computer program product comprising a non-transitory computer readable medium having a computer readable program embodied therein, wherein the computer readable program, when executed on a computing device, causes the computing device to: personalize a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF; optimize the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration by: calculating a muscle torque $\tau_m$ indicative of a muscle force based on a moment arm $\lfloor R(q) \rfloor$, wherein q represent a joint angle, an activation value a obtained from a muscle Electromyography (EMG) data, a normalized length l and a normalized velocity $\dot{l}$ of each muscle actuator in the set of muscle actuators; calculating a joint torque indicative of loading on each of the three joints, wherein the joint torque is based on an acceleration $\ddot{q}$ due to the joint torque $\tau$, the joint angle q, an inertia tensor function Q, a mass matrix M, a Coriolis component C, a gravity component G and an external force F applied to the neuromusculoskeletal arm model; generating a trajectory associated with a corresponding motion profile for each of the one or more motion tasks based on forward dynamics using the calculated muscle torque and the calculated joint torque; and evaluating a mean square error between the generated trajectory and a target trajectory associated with a corresponding motion profile for each of the one or more motion tasks; until the evaluated mean square error is less than a predefined threshold; and identify the set of the muscle actuators with the reduced number of muscle actuators at the end of the iterative steps as the optimized set of muscle actuators to perform the one or more motion tasks.

In accordance with an embodiment of the present disclosure, the one or more hardware processors are further configured to calculate the muscle torque represented by the equation $\tau_m = \lfloor R(q) \rfloor f(a,l,\dot{l})$; and further calculate the joint torque represented by the equation $\ddot{q} = [M(Q)]^{-1}\{\tau + C((q,\dot{q}) + G(q) + F)\}$, wherein $\dot{q}$ represents joint velocity.

In accordance with an embodiment of the present disclosure, the one or more hardware processors are further configured to estimate an optimal muscle synergy corresponding to the one or more motion tasks using Non-Negative Matrix Factorization (NNMF); reconstruct the muscle EMG data using the estimated optimal muscle synergy to obtain a synergy reconstructed EMG data; generate an activation map for each of the one or more motion tasks based on the synergy reconstructed EMG data, wherein the activation map is an aggregation of the activation value a of each of the muscle actuators in the optimized set of muscle actuators; and regenerate the trajectory associated with a corresponding motion profile for each of the one or more motion tasks based on the forward dynamics by providing the generated activation map for each of the one or more motion tasks to the personalized musculoskeletal arm model.

In accordance with an embodiment of the present disclosure, the one or more hardware processors are configured to estimate an optimal muscle synergy by deriving a synergy space for each of the one or more motion profiles by performing: computing number of commands needed for controlling the optimized set of muscle actuators based on the NNMF using a matrix Z of the reconstructed EMG data of muscle actuators in the optimized set of muscle actuators, wherein $Z \in X^{m*t}$, 'm' and 't' represent number of muscle actuators and number of time data, respectively such that Z=WC+E, wherein $W \in X^{m*n}$, W is a normalized row vector: $|W^i|=1$ and $W^i \in X^m$ and defines a synergy space, n is the number of control commands, n<m, and $C \in X^{n*t}$, C is a column matrix containing n commands to control m muscle actuators in the synergy space, $E \in X^{m*t}$, E is an error between Z and WC; and determining the optimal muscle synergy based on a similarity index $$L = 100\left(1 - \frac{1}{m}\sum_{i=1}^{m} \frac{\sqrt{\frac{1}{t}\sum_{j=1}^{t} E_{ij}^2}}{\sqrt{\frac{1}{t}\sum_{j=1}^{t} Z_{ij}'^2}}\right)$$

where, Z'=WC, and $E_{ij}$ and $Z_{ij}$ are the elements of matrices E and Z, respectively.

In accordance with an embodiment of the present disclosure, the one or more hardware processors are configured to calculate muscle energy consumption based on the equation:

$$E_M = \sum_{1}^{m} \frac{P_m}{t}$$

where $P_m$ represents muscle power according to $P_m = \tau_m \cdot \dot{q}$, m represents the number of muscle actuators and M denotes motion.

In accordance with an embodiment of the present disclosure, the one or more hardware processors are further configured to compute a cost function J representative of muscular effort at each time instant for m number of muscle actuators using the activation value a for each motion profile associated with each of the one or more motion tasks, wherein the cost function is represented as $J = \sum_{i=1}^{m} a_i^2$; rank a trajectory associated with each motion profile associated with each of the one or more motion tasks based on the computed cost function J; identify a motion profile associated with each of the one or more motion tasks having a minimum value for the cost function J as an optimized trajectory; and select from a repository, a neuromotor rehabilitation therapy corresponding to the identified optimized trajectory for each of the one or more motion tasks, wherein the optimized trajectory is indicative of optimal positioning of joint and muscle activation.

In accordance with an embodiment of the present disclosure, the one or more hardware processors are further configured to: calculate muscle energy consumption $E_M$ from the muscle force $\tau_m$ and the joint velocity q for the corresponding one or more motion tasks associated with the regenerated trajectory; rank, the generated trajectory associated with each of the one or more motion tasks based on the calculated muscle energy consumption $E_M$; identify the regenerated trajectory associated with each of the one or more motion tasks having a minimum value for the muscle energy consumption $E_M$ as an optimized trajectory; and select from a repository, a neuromotor rehabilitation therapy corresponding to the identified optimized trajectory for each of the one or more motion tasks, wherein the identified optimized trajectory is indicative of optimal positioning of joint and muscle activation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
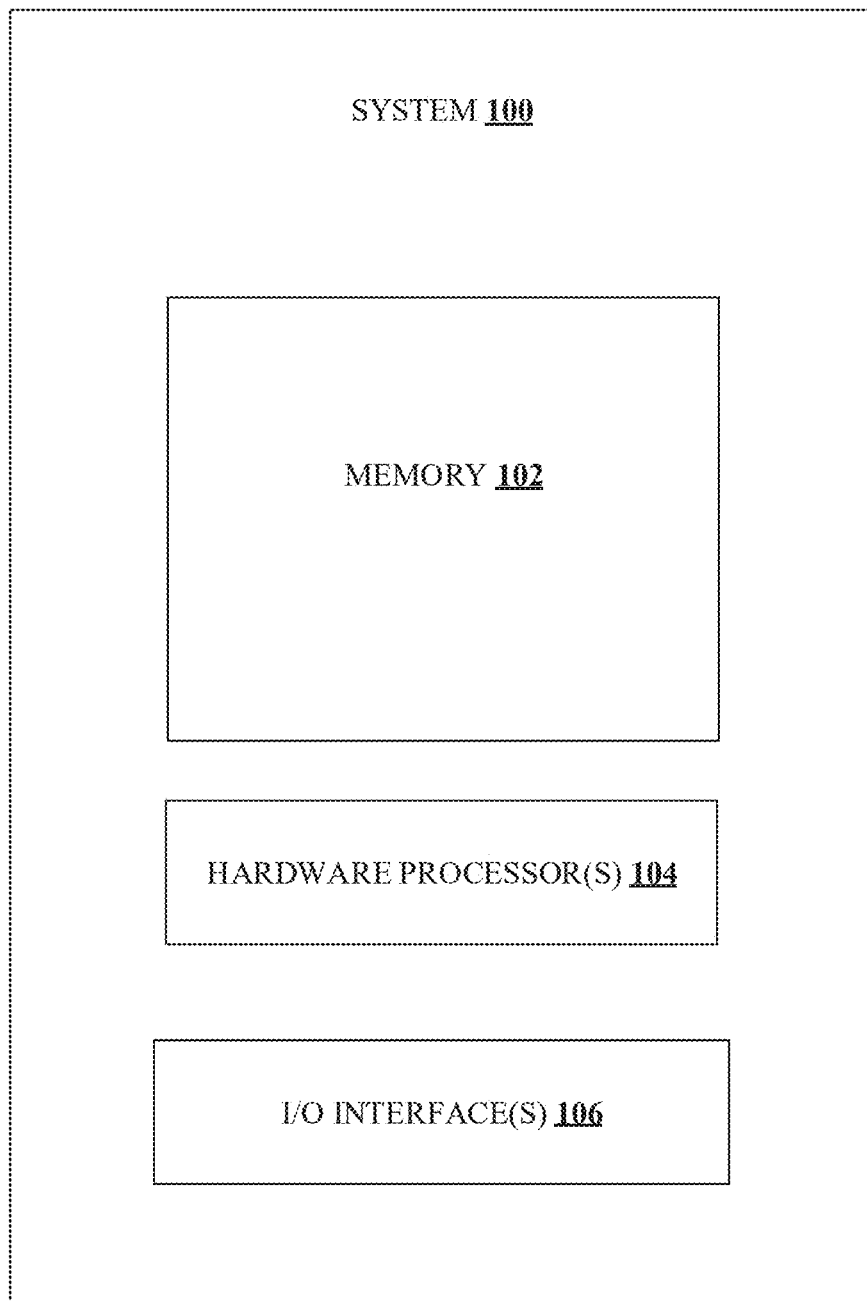
FIG. 1 illustrates a block diagram of a system that provides a personalized neuromotor rehabilitation therapy for upper limb using a neuromusculoskeletal arm model, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Conventional methods that work with neural dynamics in deriving muscle synergy are dependent on single tasks, leaving synergy variation with task variability unexplored. An important application related to synergy variation is in study of post stroke movement alteration, where knowledge of muscle synergy can be used to determine simplifying motor control mechanism for altered movement generation and in rehabilitation. Several state of art methods exist for synergy control mechanism in post stroke rehabilitation during hand reaching task execution. However, a clear understanding of the workspace, task variable and synergy paradigm is required to derive conclusive control actions to particularly aid in rehabilitation.

Applicant has addressed the problem of providing a personalized neuromotor rehabilitation therapy for upper limb using a neuromusculoskeletal arm model. The neuromusculoskeletal arm model is personalized based on anthropometric measurements and then the model is further adapted to be operated with an optimized set of muscle actuators. Use of a simulation platform to test motion and generate activation in place of real Electromyography (EMG) data provides the flexibility to test different task combinations theoretically, before finding an optimal energy task space for different motion tasks. The synergy space configuration and energy optimized trajectory generated by the method and system of the present disclosure facilitates planning a personalized rehabilitation therapy for patients with neuromotor disabilities such as post stroke patients and may also help in better control of neuro-prosthetic arms.

In the context of the present disclosure, the neuromusculoskeletal arm model may interchangeably be referred as musculoskeletal arm model or arm model. The musculoskeletal arm model in the present disclosure is a simplified adaptation of an Holzbaur model, capturing the dynamics of glenohumeral joint for specific point to point reaching task involving active elbow flexion.

Referring now to the drawings, and more particularly to FIG. 1 through FIG. 8C, where similar reference characters denote corresponding features consistently throughout the figures, there are shown preferred embodiments and these embodiments are described in the context of the following exemplary system and/or method.

FIG. 1 illustrates an exemplary block diagram of a system 100 that provides a personalized neuromotor rehabilitation therapy for upper limb using a neuromusculoskeletal arm model, in accordance with some embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
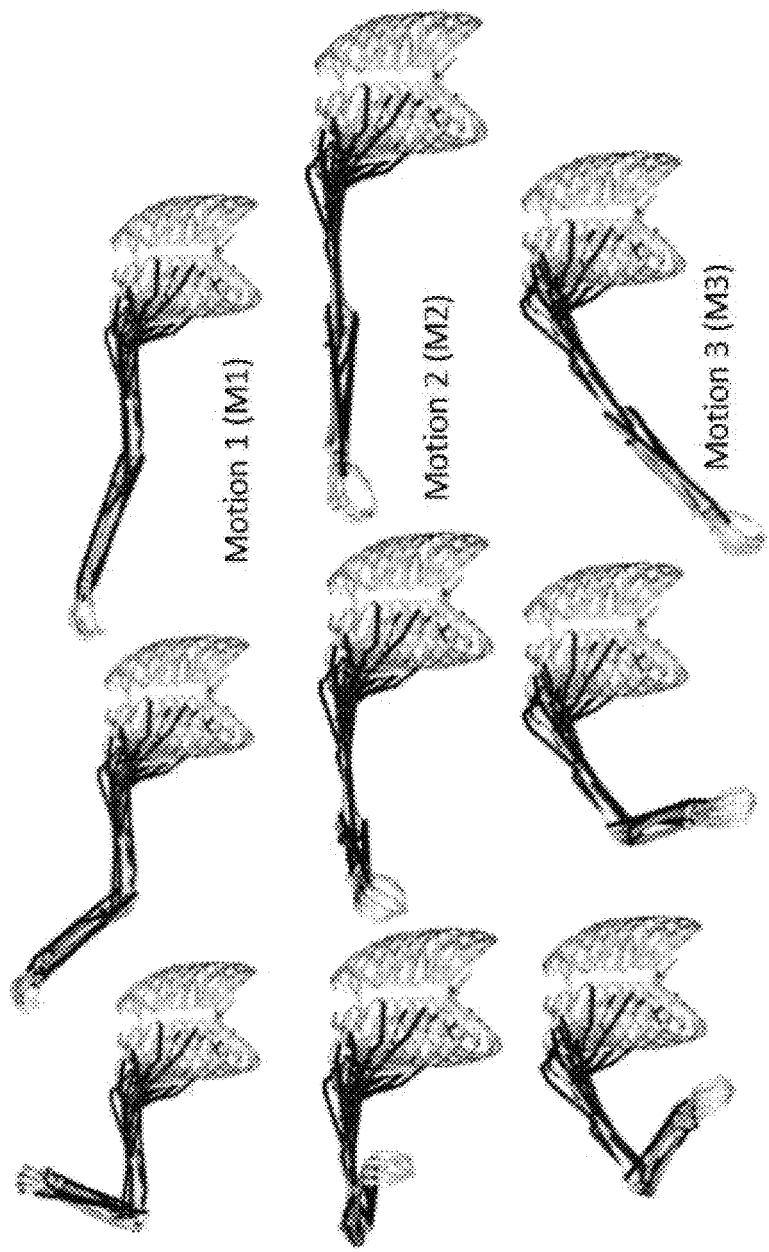
FIG. 2 illustrates three exemplary hand reach motions considered in the present disclosure.

FIG. 2 illustrates three exemplary hand reach motions (M1, M2, M3) considered in the present disclosure for explaining the workflow of a method that provides a personalized neuromotor rehabilitation therapy for upper limb using a neuromusculoskeletal arm model. The three motions resemble point to point reaching task in a three-dimensional plane, keeping trajectory of elbow joint fixed in all three motions. These motions resemble routine exercise motion to regain joint operative range of motion after stroke or any rehabilitation specific to neuro-motor disorder. Motion variation was in terms of change in shoulder configuration, i.e. change in elevation angle (flexion-extension) and rotation (internal-external). The other degree of freedom, i.e., shoulder abduction-adduction was fixed. Numerically solving, there can be infinite joint configuration in the three-dimensional plane to complete a reach task and in practice the developed arm model is suitable to generate all possible joint configurations.

Exemplary point to point hand reach motions with joint configuration values and range of motion are provided in the TABLE 1 below. It may be understood by those skilled in the art, that the exemplary hand reach motions are non-limiting motion tasks that may be performed by a subject and the method and system of the present disclosure may be extended to other motion tasks.

TABLE 1

Point to point hand reach motions with joint configuration values and range of motion

| Motion | Shoulder abduction-adduction | Shoulder flexion-extension | Shoulder internal-external rotation | Elbow flexion |
|---|---|---|---|---|
| M1 | 0 degree | 90 degree | −45 degree | 0-105 degree |
| M2 | 0 degree | 90 degree | 0 degree | 0-105 degree |
| M3 | 0 degree | 90 degree | 20 degree | 0-105 degree |

Figure 3:
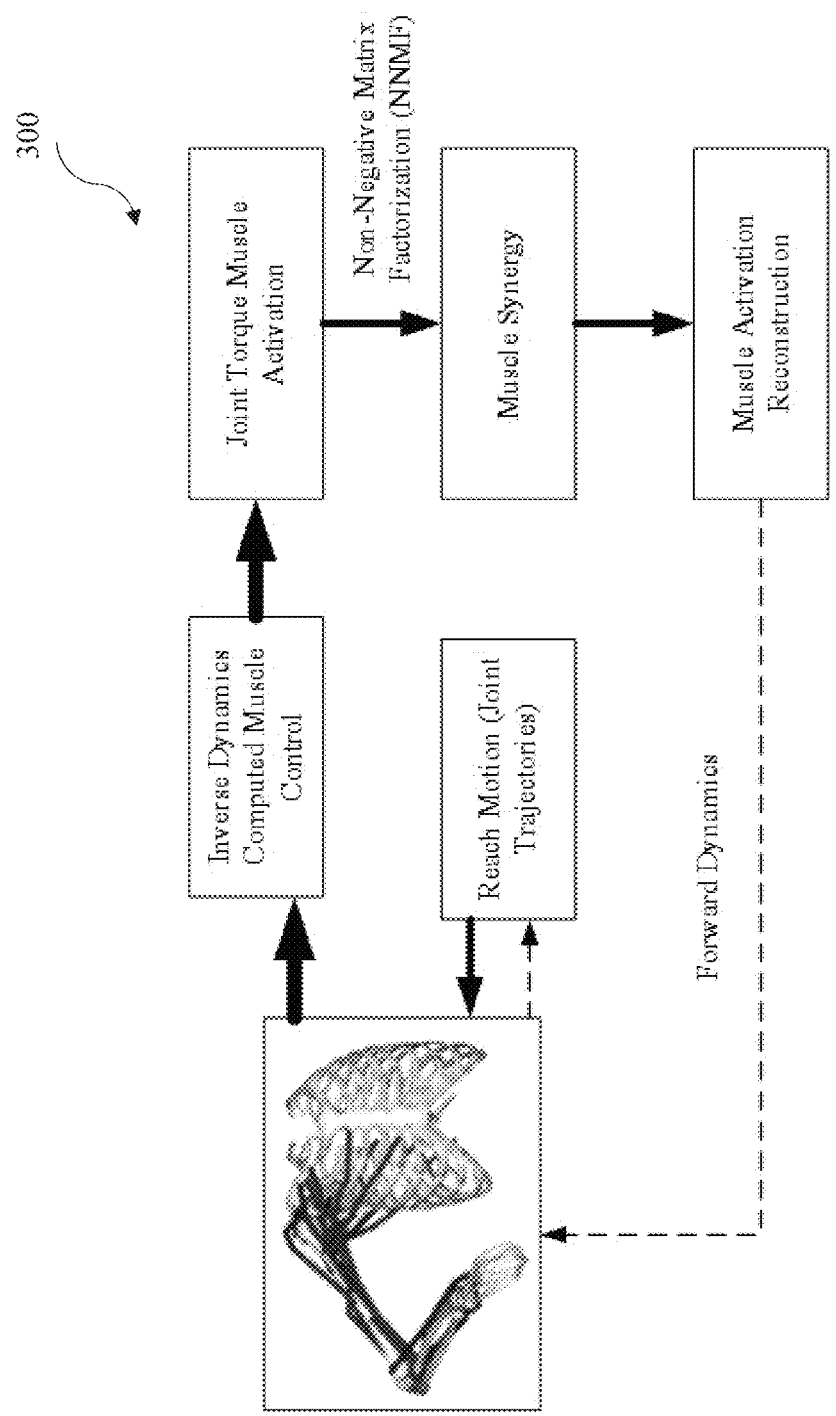
FIG. 3 is an exemplary high level flow diagram illustrating a general workflow of a method that provides the personalized neuromotor rehabilitation therapy for upper limb using the neuromusculoskeletal arm model, in accordance with some embodiments of the present disclosure.
Figure 4A:
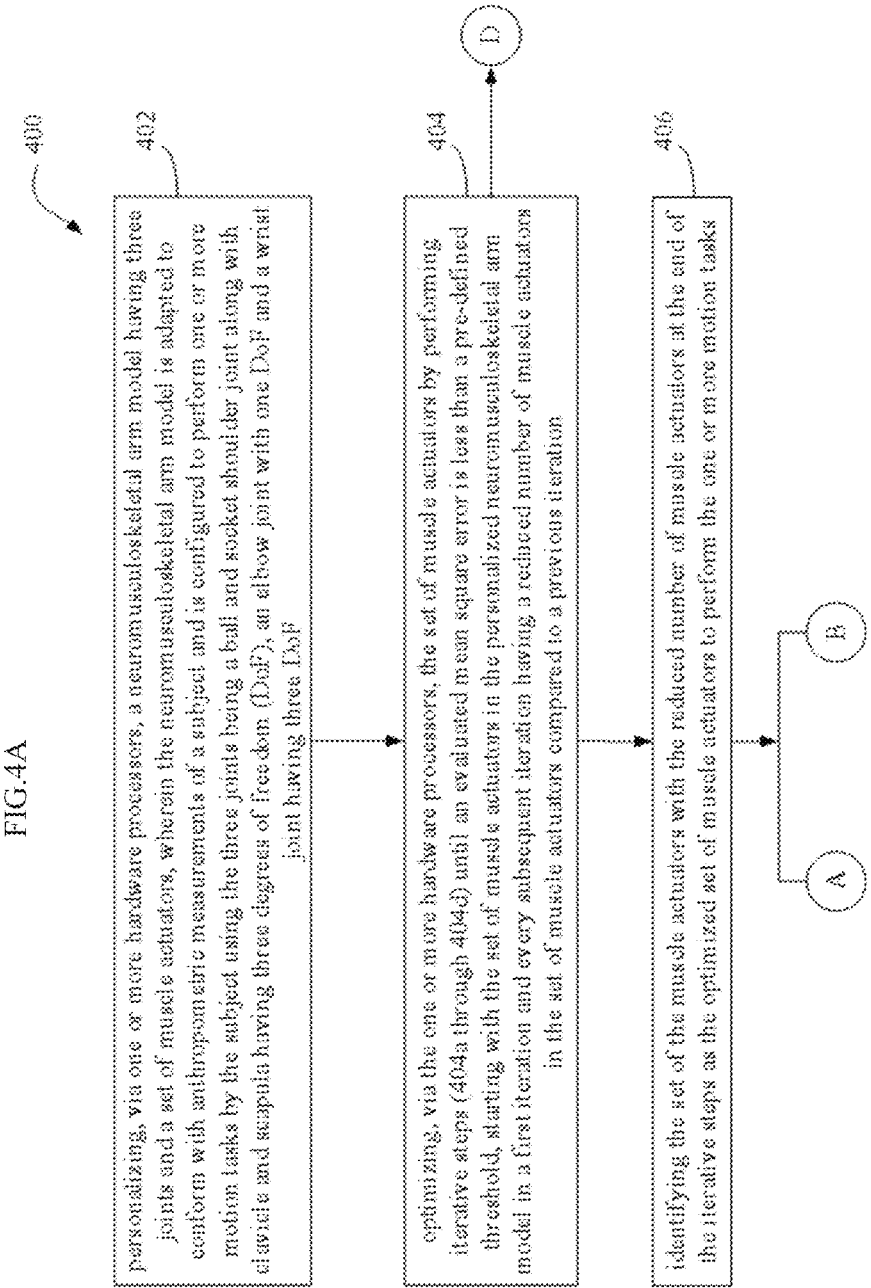
FIG. 4A is a first part of an exemplary flow diagram of a computer implemented method that provides the personalized neuromotor rehabilitation therapy for upper limb using the neuromusculoskeletal arm model, in accordance with some embodiments of the present disclosure.
Figure 4B:
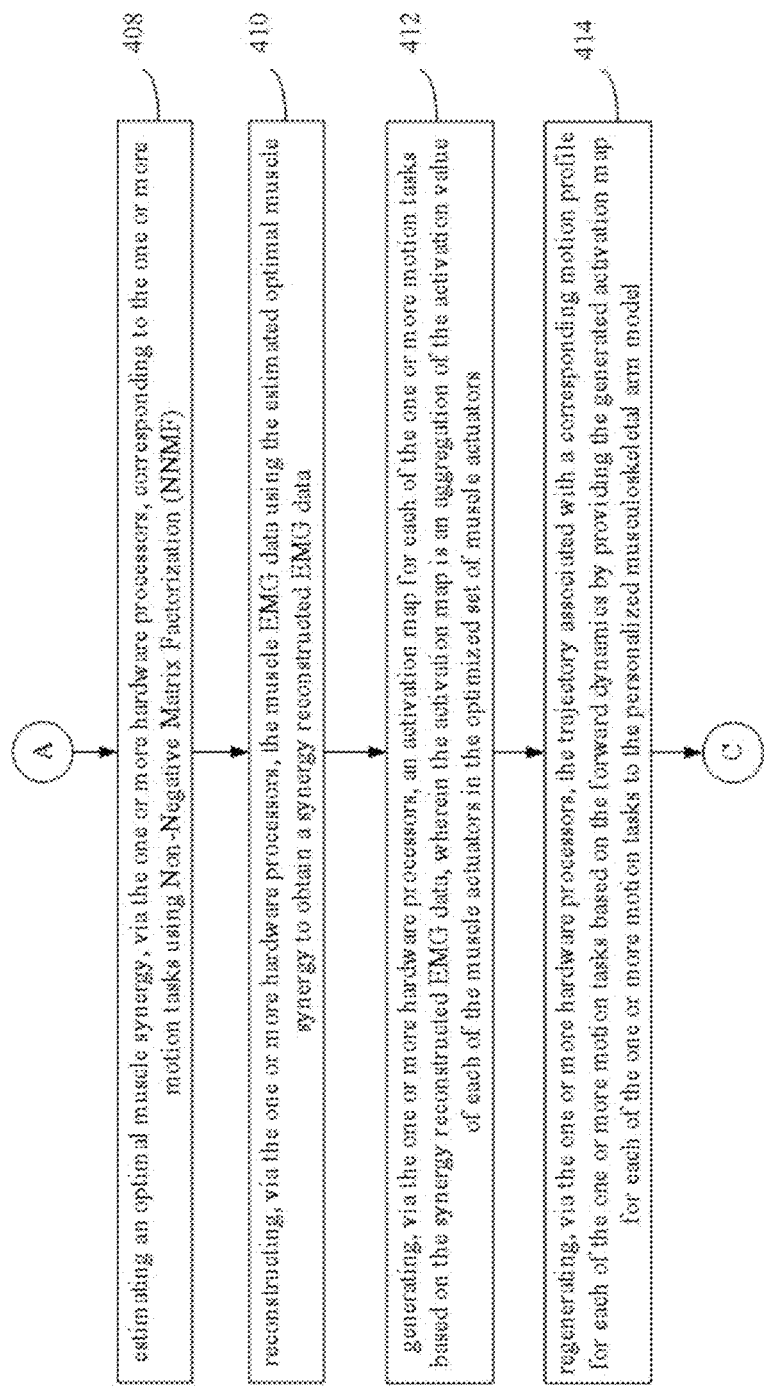
FIG. 4B is a second part of an exemplary flow diagram of a computer implemented method that provides the personalized neuromotor rehabilitation therapy for upper limb using the neuromusculoskeletal arm model, in accordance with some embodiments of the present disclosure.
Figure 4C:
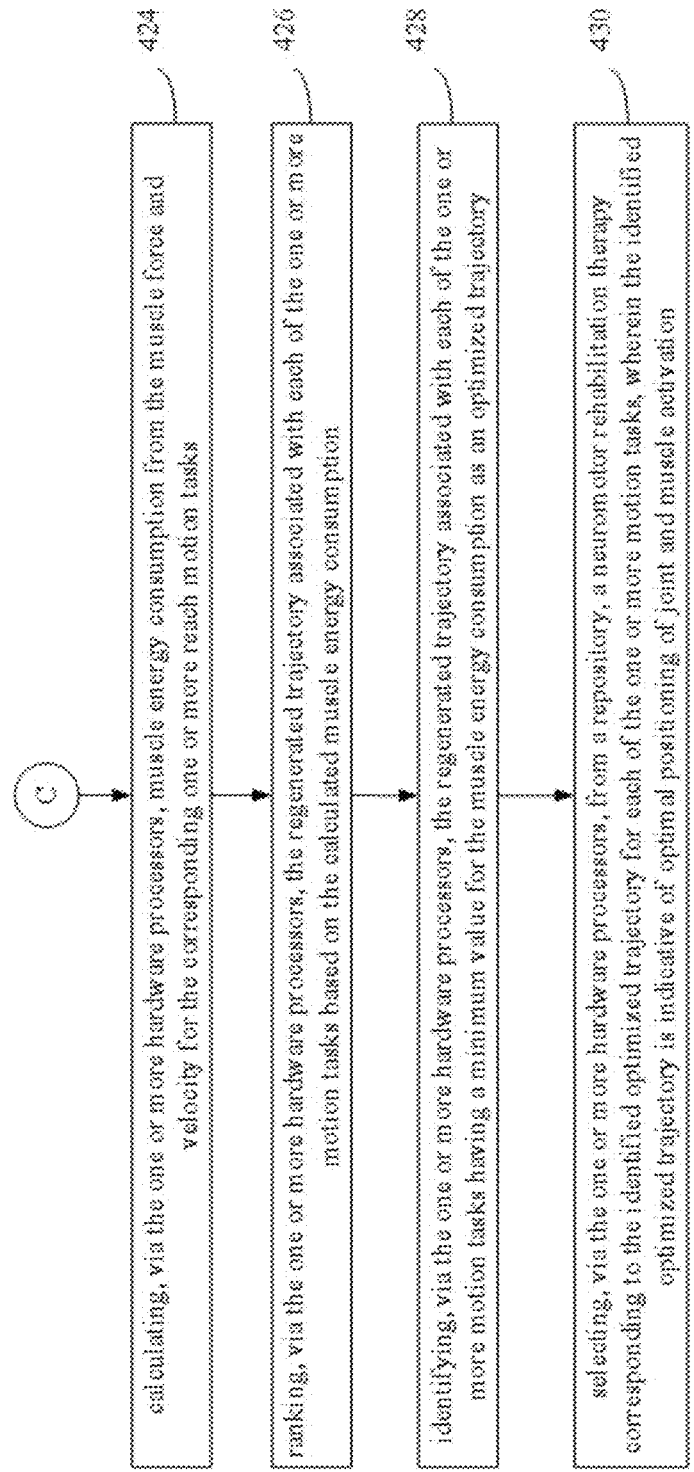
FIG. 4C is a third part of an exemplary flow diagram of a computer implemented method that provides the personalized neuromotor rehabilitation therapy for upper limb using the neuromusculoskeletal arm model, in accordance with some embodiments of the present disclosure.
Figure 4D:
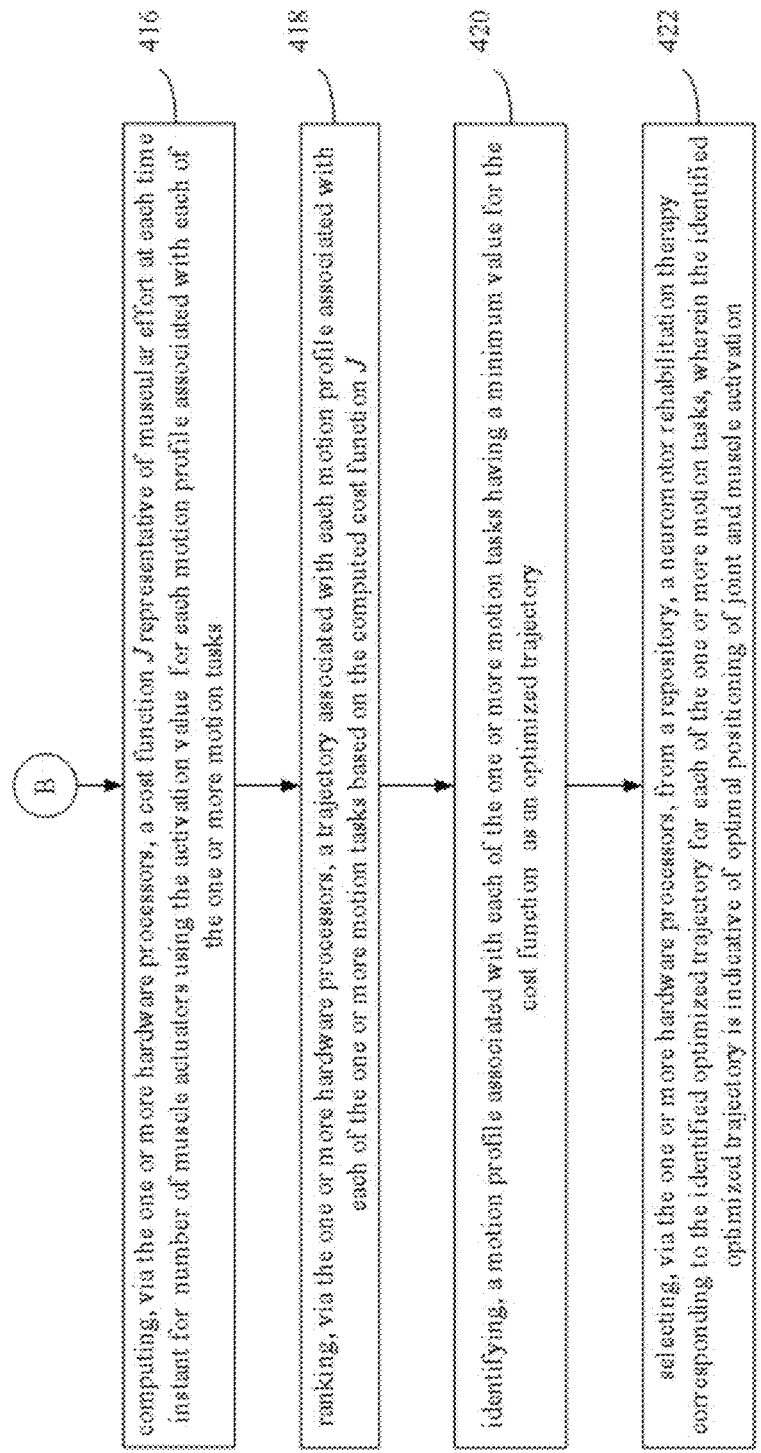
FIG. 4D is a fourth part of an exemplary flow diagram of a computer implemented method that provides the personalized neuromotor rehabilitation therapy for upper limb using the neuromusculoskeletal arm model, in accordance with some embodiments of the present disclosure.
Figure 4E:
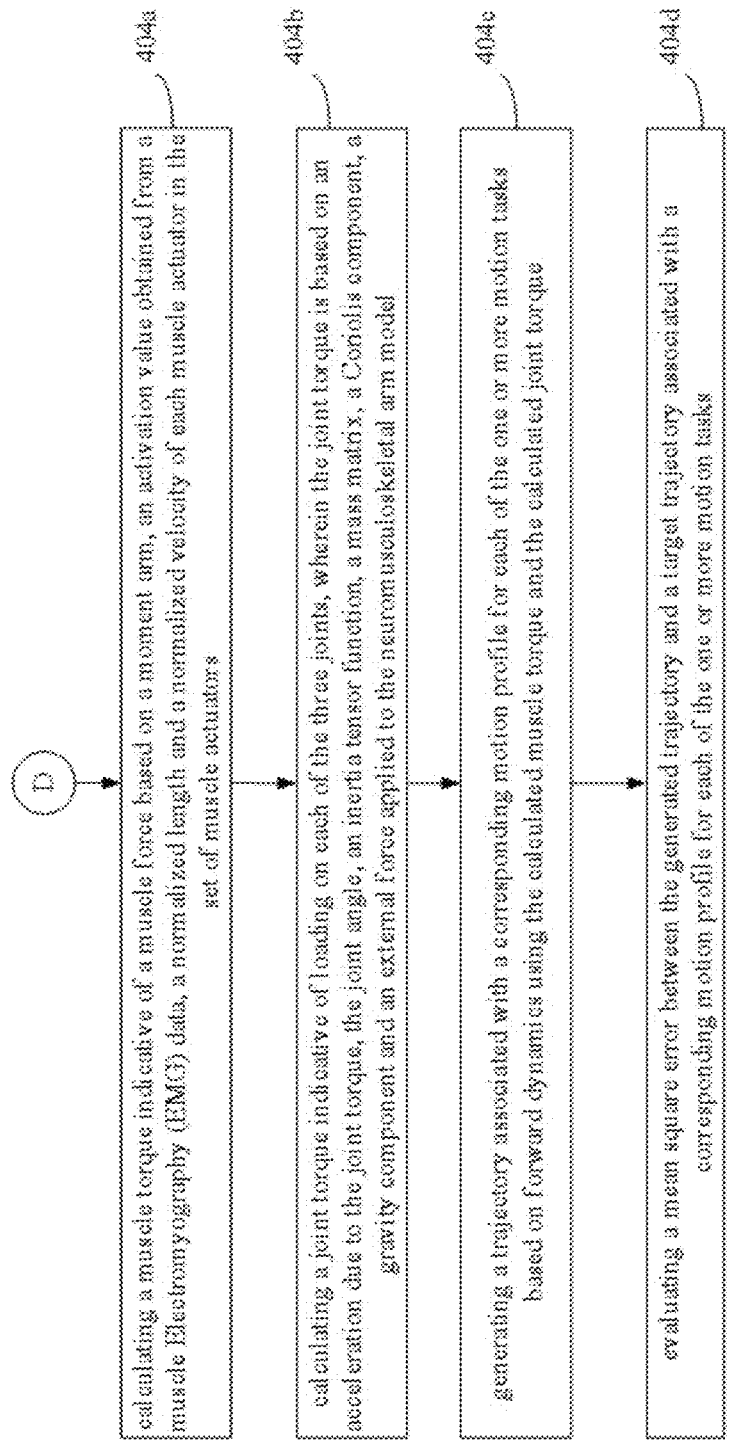
FIG. 4E is a fifth part of an exemplary flow diagram of a computer implemented method that provides the personalized neuromotor rehabilitation therapy for upper limb using the neuromusculoskeletal arm model, in accordance with some embodiments of the present disclosure.

FIG. 3 is an exemplary high level flow diagram 300 illustrating a general workflow of a method that provides a personalized neuromotor rehabilitation therapy for upper limb using a neuromusculoskeletal arm model, in accordance with some embodiments of the present disclosure. The neuromusculoskeletal arm model with an optimized set of muscle actuators is fed with target (desired) trajectories associated with the three exemplary hand reach motions (M1, M2, M3). A muscle force and a joint torque are calculated through inverse dynamics and computed muscle control. From muscle activation for the optimized set of muscle actuators, muscle synergy is estimated using Non-Negative Matrix Factorization (NNMF). Muscle Electromyography (EMG) data is reconstructed. From a generated activation map corresponding to the reconstructed EMG data, forward dynamics is calculated to derive joint angles and positions corresponding to the generated activation map and is fed to the arm model. Error function may then be calculated based on a targeted trajectory and the trajectory calculated from a synergy space.

FIG. 4A through FIG. 4E illustrate an exemplary flow diagram of a computer implemented method 400 that provides the personalized neuromotor rehabilitation therapy for upper limb using the neuromusculoskeletal arm model, in accordance with some embodiments of the present disclosure. In an embodiment, the system 100 includes one or more data storage devices or memory 102 operatively coupled to the one or more processors 104 and is configured to store instructions configured for execution of steps of the method 400 by the one or more processors 104. The steps of the method 400 will now be explained in detail with reference to the components of the system 100 of FIG. 1 and the high level flow diagram 300 using the exemplary hand reach motions of FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Accordingly, in an embodiment of the present disclosure, the one or more processors 104, are configured to personalize, at step 402, a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF. The anthropometric measurements of the subject may include height, weight, triceps and mid-upper-arm circumference that provides a proxy measure of body composition (e.g. muscularity, fat free mass and fat mass).

An exemplary neuromusculoskeletal arm model is a simplified adaptation of Holzbaur model provided by Holzbaur, K. R., et al., *Moment-generating capacity of upper limb muscles in healthy adults. Journal of Biomechanics* (2006) for capturing the dynamics of glenohumeral joint for specific point to point reaching task involving active elbow flexion. In the exemplary arm model used in the present disclosure, the set of muscle actuators included 49 muscle actuators having 23 DoF.

Dynamic characteristics of the arm model is dependent on muscle characteristics. In OpenSim, 'Hill type' muscle property is defined using the 'Thelen 2003' muscle model, comprising of a contractile element (CE), a parallel element (PE), and a series element (SE). Muscle force generated from the 'Thelen' muscle actuator is a function of three factors: activation value (a), normalized length of the muscle unit (I), and normalized velocity of the muscle unit ('I). Individual muscles can be characterized by some parameters like pennation angle, contraction velocity, muscle fibre length, tendon slack length, maximum isometric force, etc. These parameters may be selected to desired value as per requirement, or if data is available, model can even be personalized with specific muscle properties. In an embodiment, the muscle actuators may be one of Hill type, modified hill type, Huxley model, Zajac model, and the like and in an embodiment the personalizing of the neuromusculoskeletal arm model may employ a scaling function by OpenSim.

In an embodiment of the present disclosure, the one or more processors 104, are configured to optimize, at step 404, the set of muscle actuators (49 in an exemplary embodiment) by performing the following iterative steps starting with the set of muscle actuators in the personalized neuromusculoskeletal arm model in a first iteration and every subsequent iteration having a reduced number of muscle actuators in the set of muscle actuators compared to a previous iteration until an evaluated mean square error is less than a pre-defined threshold. The iterative steps include steps 404a through 404d described hereinafter. At step 404a, a muscle torque $\tau_m$ indicative of a muscle force based on a moment arm $\lfloor R(q) \rfloor$ wherein q represent a joint angle, an activation value a obtained from a muscle Electromyography (EMG) data, a normalized length l and a normalized velocity $\dot{l}$ of each muscle actuator in the set of muscle actuators is calculated.

Computing the activation value a: In simulation studies, a muscle model is an algorithm transforming muscle activation into muscle force. At a given time t in a simulation, the muscle model's inputs are activation a (a real number between 0 and 1 inclusive) and length l of the muscle actuator. The muscle model's output is the muscle-tendon actuator force. Activation dynamics represent how an excitation, a unit-less value between 0 and 1 is transformed into an activation that is also a unit-less value between 0 and 1, of a muscle. When a muscle is neurally excited, its activation gradually increases, while if a muscle's excitation decreases, its activation also decreases, albeit at a slower rate than the increase.

At step 404b, a joint torque indicative of loading on each of the three joints is calculated, wherein the joint torque is based on an acceleration $\ddot{q}$ due to the joint torque $\tau$, the joint angle q, an inertia tensor function Q, a mass matrix M, a Coriolis component C, a gravity component G and an external force F applied to the neuromusculoskeletal arm model.

In an embodiment, the step of calculating the muscle torque is represented by the Thelen model equation:

$$\tau_m = \lfloor R(q) \rfloor f(a, l, \dot{l}) \quad \rightarrow (1)$$

In an embodiment, the step of calculating the joint torque is represented by the equation:

$$\ddot{q} = [M(Q)]^{-1}\{\tau + C((q, \dot{q}) + G(q) + F)\} \quad \rightarrow (2)$$

wherein $\dot{q}$ represents joint velocity.

At step 404c, a trajectory associated with a corresponding motion profile for each of the one or more motion tasks based on forward dynamics using the calculated muscle torque and the calculated joint torque is generated. In an embodiment, a 5th-order Runge-Kutta-Feldberg integrator is used to solve (numerically integrate) the dynamical equations for the trajectories of the arm model states over a definite interval in time generating the trajectory.

At step 404d, a mean square error between the generated trajectory and a target trajectory associated with a corresponding motion profile for each of the one or more motion tasks is evaluated. The target trajectory or the desired trajectory may be a point to point motion associated the task as shown in FIG. 2.

Figure 5:
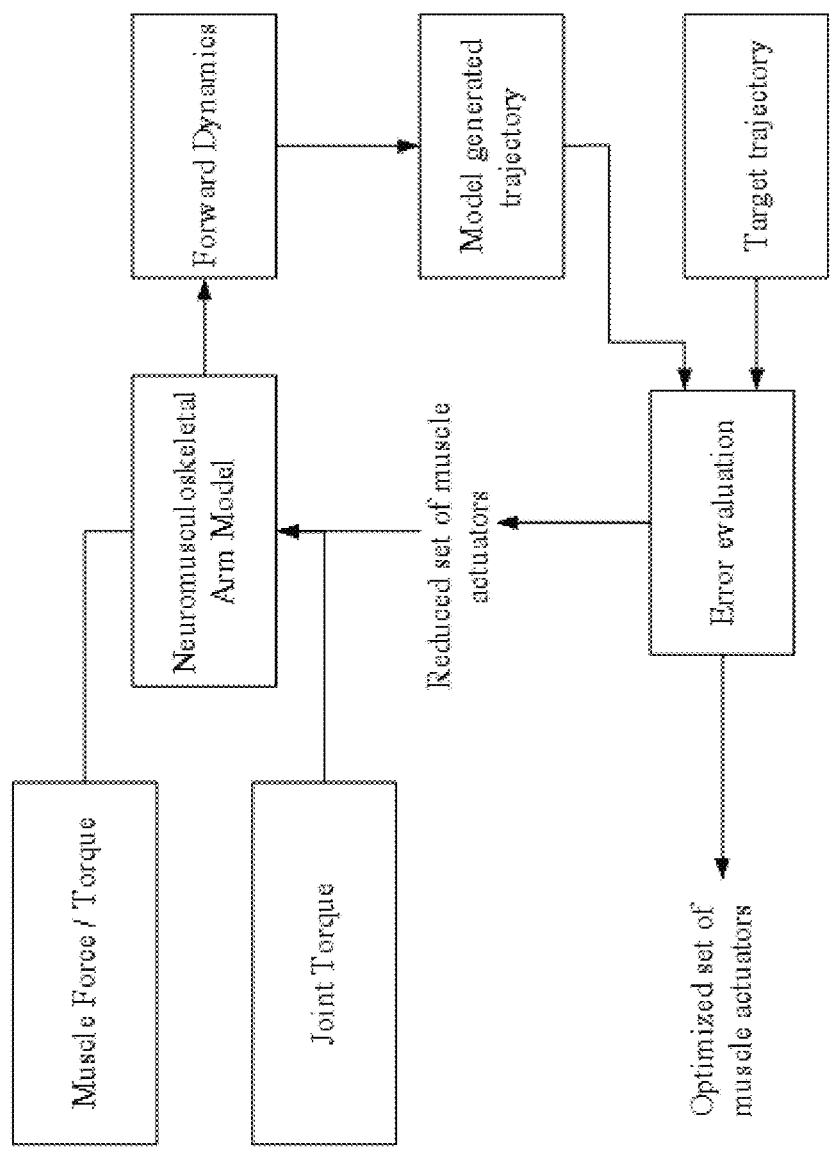
FIG. 5 is an exemplary flow diagram illustrating steps for identifying an optimized set of muscle actuators in the musculoskeletal arm model in the method of FIG. 4A through FIG. 4E, in accordance with some embodiments of the present disclosure.

In an embodiment of the present disclosure, the one or more processors 104, are configured to identify, at step 406, the set of the muscle actuators with the reduced number of muscle actuators at the end of the iterative steps as the optimized set of muscle actuators to perform the one or more motion tasks. In an embodiment, the optimized set of muscle actuators include a reduced set of 27 'hill type' muscle actuators (from the 49 muscle actuators) distributed in three groups of 14 muscle actuators controlling the shoulder joint, 9 muscle actuators for the elbow joint and 4 muscle actuators controlling a forearm with wrist movement. The distribution of muscle actuators into groups is based on the type of motion task to be performed by the subject. FIG. 5 is an exemplary flow diagram illustrating steps for identifying an optimized set of muscle actuators in the musculoskeletal arm model, in accordance with some embodiments of the present disclosure.

The pre-defined threshold for the evaluated mean square error depends on the subject and the motion task performed. In an embodiment, the mean square error may be 2% for the three exemplary reach motions illustrated in FIG. 2.

Having identified the optimized set of muscle actuators, the next step involves estimating muscle synergy. In time-dependent approach, muscle synergy constitutes the coordinated activation of groups of muscles with fixed time-varying profile. For time independent formulation, as in the present disclosure, fixed weights, capable of creating a new work space of reduced dimension are associated with muscle activation. Accordingly, in an embodiment of the present disclosure, the one or more processors 104, are configured to estimate an optimal muscle synergy, at step 408, corresponding to the one or more motion tasks using the NNMF. The muscle EMG data is then reconstructed, at step 410, using the estimated optimal muscle synergy to obtain a synergy reconstructed EMG data. An activation map for each of the one or more motion tasks is generated based on the synergy reconstructed EMG data, at step 412, wherein the activation map is an aggregation of the activation value a of each of the muscle actuators in the optimized set of muscle actuators. The one or more processors 104, are configured to regenerate, at step 414, the trajectory associated with a corresponding motion profile for each of the one or more motion tasks based on the forward dynamics by providing the generated activation map for each of the one or more motion tasks to the personalized musculoskeletal arm model.

Muscle synergy is used to derive redundant muscle information from the optimized set of muscle actuators, which help to recreate desired motion if any of the major muscles get damaged due to motor injury. Time independent formulation is incorporated to derive synergy space for the three exemplary motions. NNMF works on a set of multivariate 'n' dimensional data vectors. Generally, for controlling m muscles, n neural commands are required. NNMF reduces the n neural commands into a low dimensional subspace. Accordingly, in an embodiment, the step of estimating an optimal muscle synergy, at step 408 comprises deriving a synergy space for each of the one or more reach motion profiles by firstly computing number of commands needed for controlling the optimized set of muscle actuators based on the NNMF using a matrix Z of the reconstructed EMG data of muscle actuators in the optimized set of muscle actuators, wherein $Z \in X^{m*t}$, 'm' and 't' represent number of muscle actuators and number of time data, respectively such that $$Z = WC + E \quad \rightarrow (3)$$

wherein $W \in X^{m*n}$, W defines a synergy space (indicate of the activation map) and is a normalized row vector: $|W^i| = 1$ and $W^i \in X^m$ n is the number of control commands, n<m, and $C \in X^{n*t}$, C is a column matrix containing n commands to control m muscle actuators in the synergy space, $E \in X^{m*t}$, E is an error between Z and WC.

Secondly, the optimal muscle synergy is determine based on a similarity index $$L = 100 \left( 1 - \frac{1}{m} \sum_{i=1}^{m} \frac{\sqrt{\frac{1}{t}\sum_{j=1}^{t} E_{ij}^2}}{\sqrt{\frac{1}{t}\sum_{j=1}^{t} Z_{ij}'^2}} \right) \rightarrow \quad (4)$$

where, Z'=WC, and $E_{ij}$ and $Z_{ij}$ are the elements of matrices E and Z, respectively. The error E, between Z and WC in equation (3) must be small enough so that m muscles may be controlled by n commands in. In an embodiment, the matrix Z is factorized using MU (multiplicative updates) method. The range of L is 0<L<100. Value of L is sensitive to the shape and magnitude of the reconstructed EMG data. Generally, value of L>75% is considered as 'good fit' to guarantee complete muscle reconstruction. Muscle energy is calculated from muscle power which is a product of muscle force and velocity.

Figure 7A:
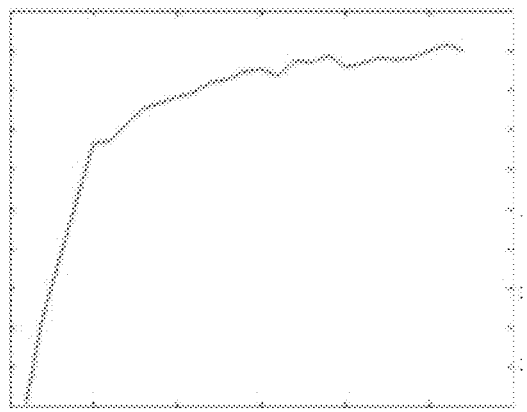
FIG. 7A illustrates a first similarity plot and muscle synergy variation for original muscle recruitment and for similarity value 85% and 75% for motion M1, M2 and M3, respectively in accordance with some embodiments of the present disclosure.
Figure 7A:
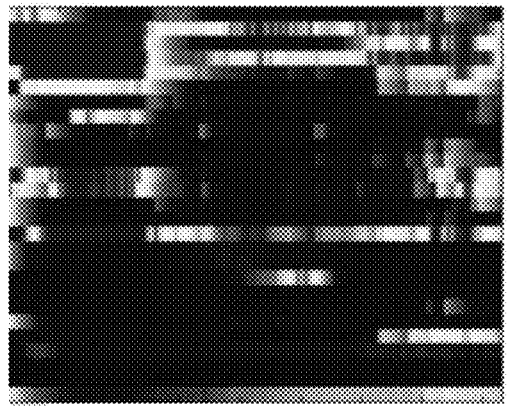
Figure 7A:
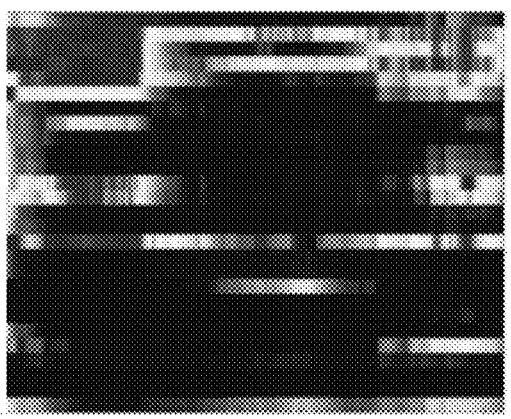
Figure 7A:
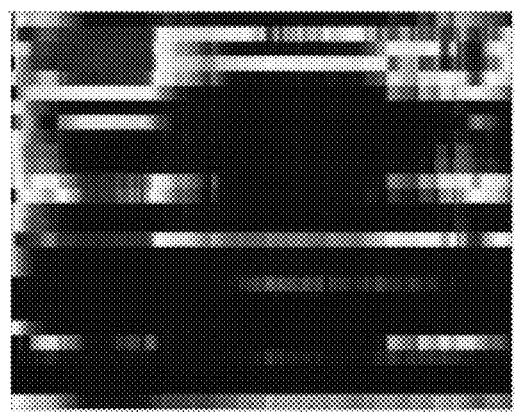
Figure 7B:
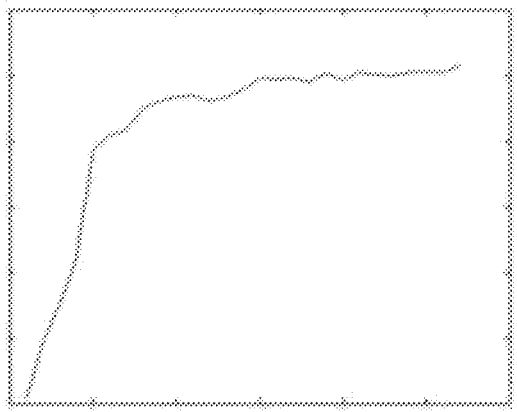
FIG. 7B illustrates a second similarity plot and muscle synergy variation for original muscle recruitment and for similarity value 85% and 75% for motion M1, M2 and M3, respectively in accordance with some embodiments of the present disclosure.
Figure 7B:
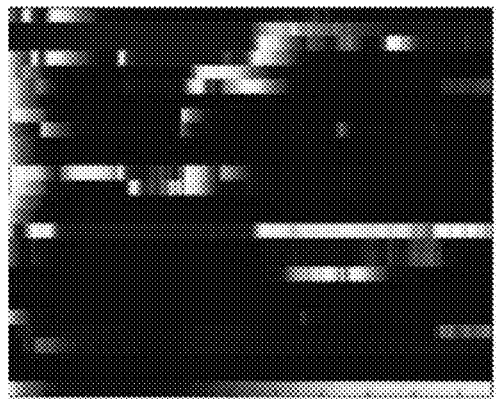
Figure 7B:
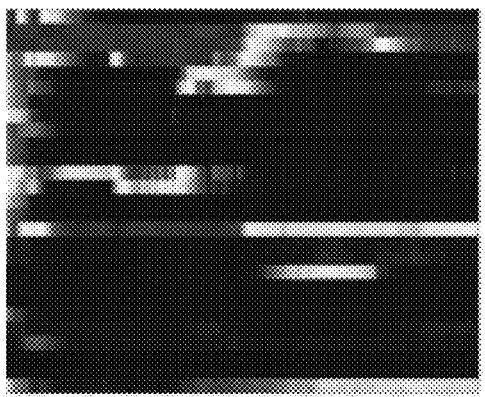
Figure 7B:
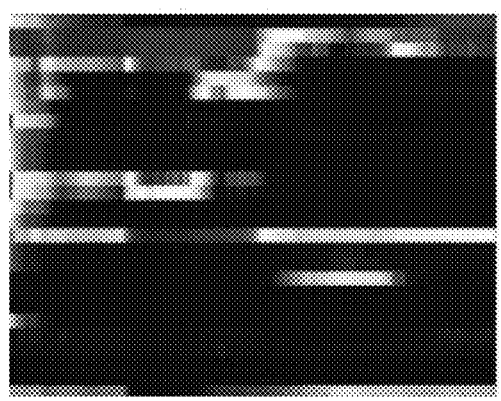
Figure 7C:
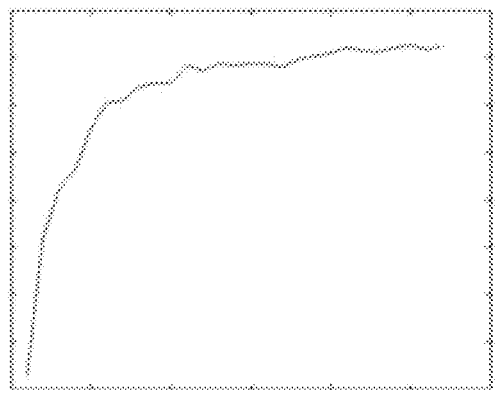
FIG. 7C illustrates a third similarity plot and muscle synergy variation for original muscle recruitment and for similarity value 85% and 75% for motion M1, M2 and M3, respectively in accordance with some embodiments of the present disclosure.
Figure 7C:
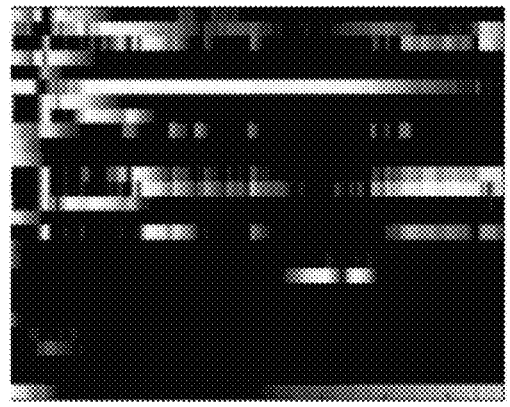
Figure 7C:
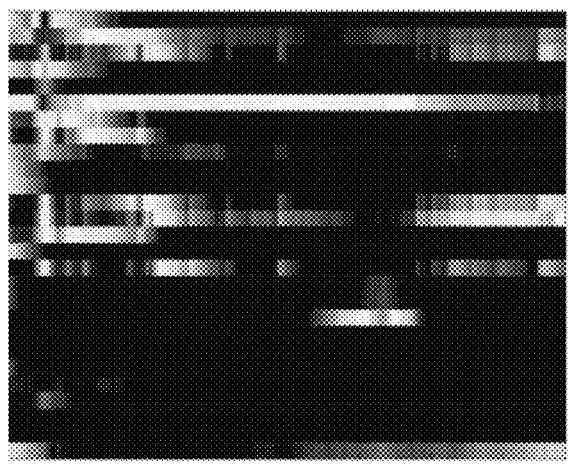
Figure 7C:
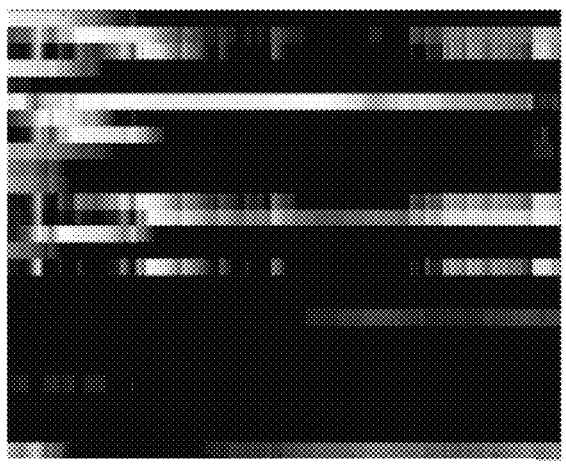

Considering the similarity index value of 75% for truthful reconstruction of activation, Motion M1 has minimum synergy value of 4, Motion M2 has synergy value of 5 and Motion M3 has synergy value of 3. For all three motions, synergy value of 8 corresponded to similarity index of 85%. Motion M3, which corresponds to a configuration due to alteration of both shoulder rotation and elevation shows minimum synergy requirement for reconstruction. FIG. 7A through FIG. 7C illustrates a similarity plot and muscle synergy variation for original muscle recruitment and for similarity value 85% and 75% for motion M1, M2 and M3, respectively in accordance with some embodiments of the present disclosure. The similarity plot illustrates similarity along the y-axis and synergy along the x-axis.

Figure 8A:
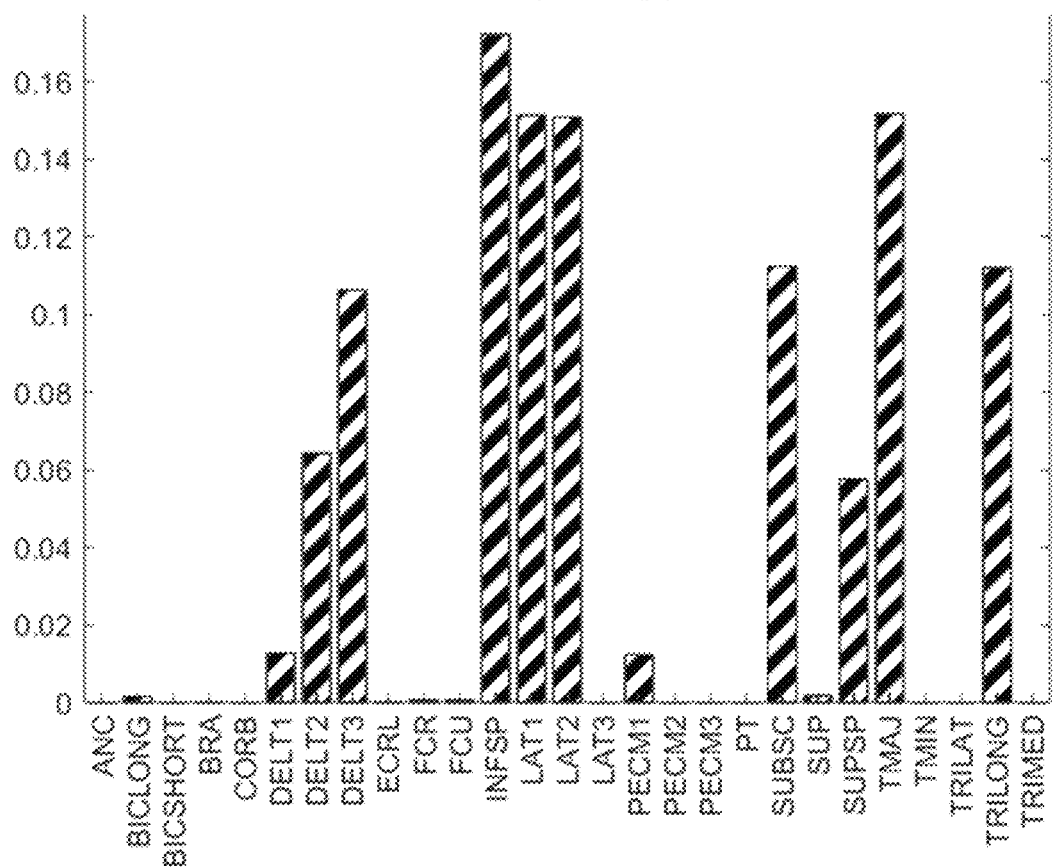
FIG. 8A illustrates a first synergy weight distribution at 85% similarity for motion M1, M2 and M3, in accordance with some embodiments of the present disclosure.
Figure 8B:
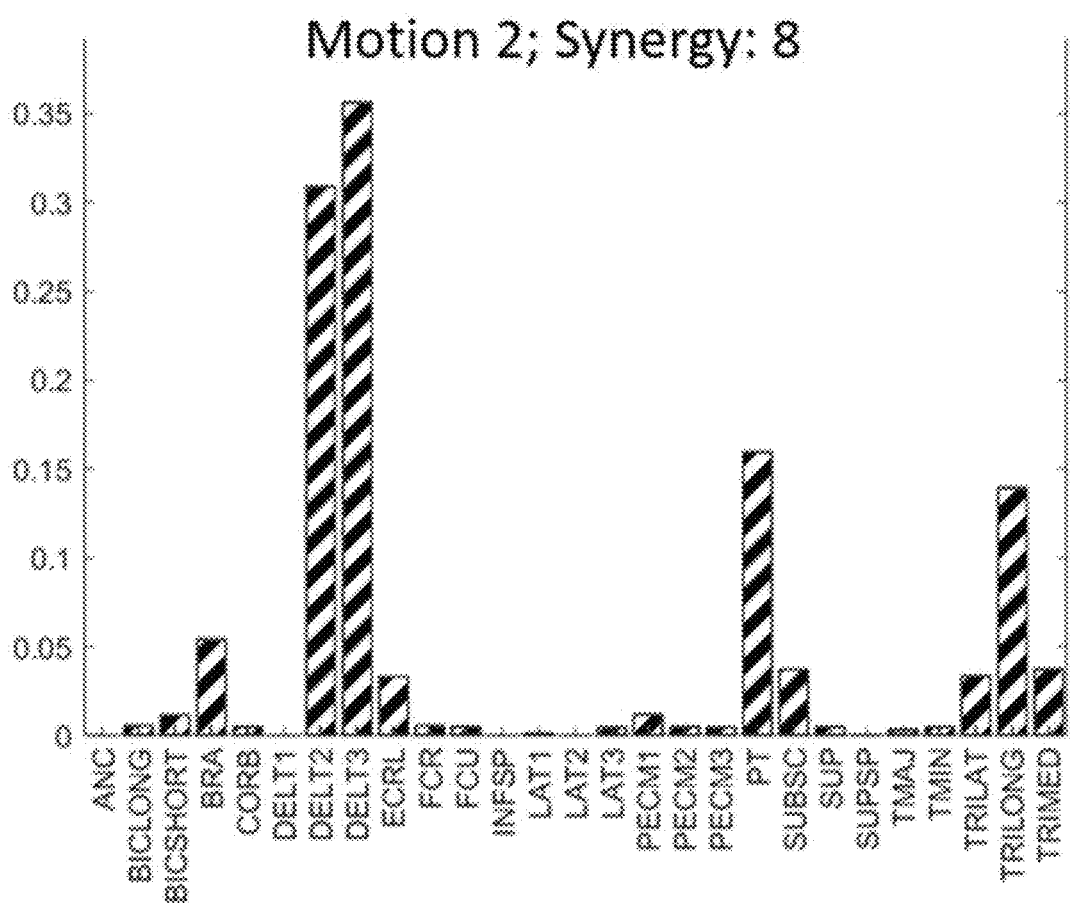
FIG. 8B illustrates a second synergy weight distribution at 85% similarity for motion M1, M2 and M3, in accordance with some embodiments of the present disclosure.
Figure 8C:
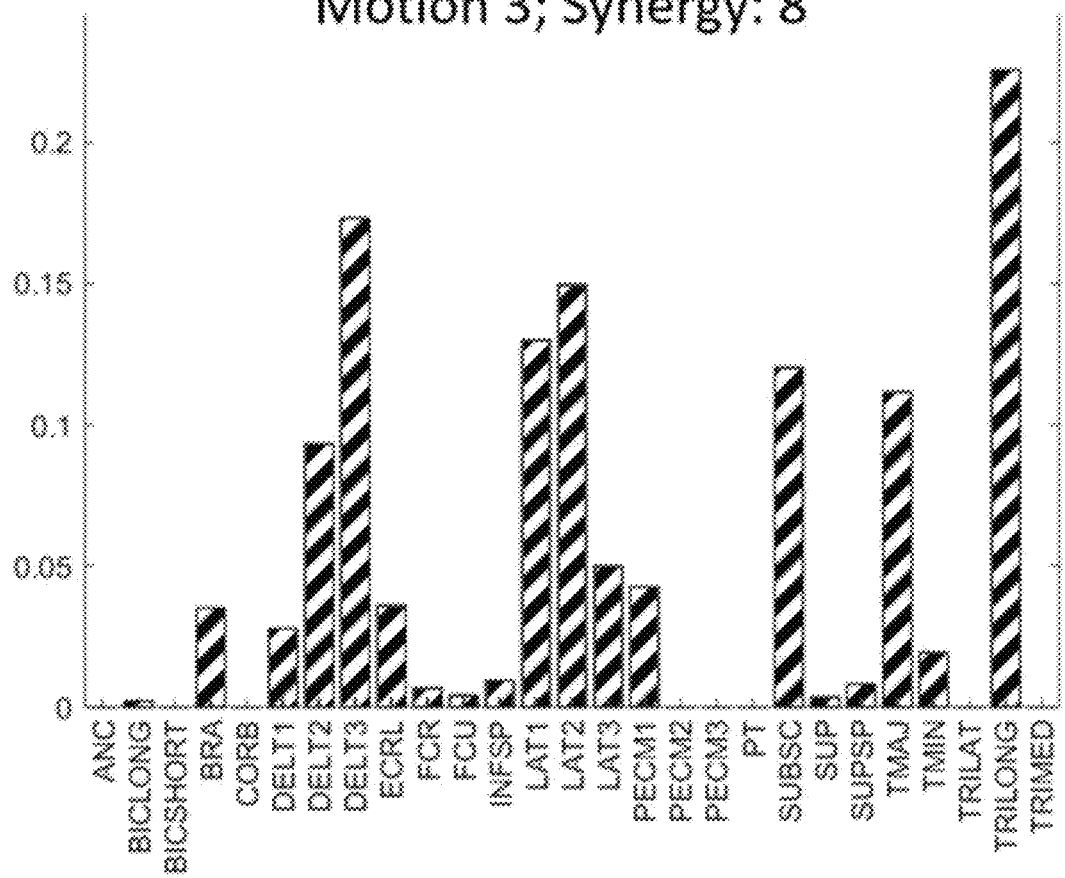
FIG. 8C illustrates a third synergy weight distribution at 85% similarity for motion M1, M2 and M3, in accordance with some embodiments of the present disclosure.

When activation is decomposed in synergy space, it is represented through individual muscle weights and a neural command. FIG. 8A through FIG. 8C illustrates synergy weight distribution at 85% similarity for motion M1, M2 and M3, in accordance with some embodiments of the present disclosure. The figures FIG. 8A through FIG. 8C show synergy weight distribution for the three motions at synergy value at 8. The weight distribution shows which muscle will have higher response for a particular neural command at a given time. Each synergy has a different activation combination across muscles, with some muscle contributing more in terms of activation than others. Also, the weight varies with change in synergy for same motion. When comparing between three motions at synergy level 8, for Motion M1, Infraspinatus (INFSP), Latissimus (LAT 1,2) are more prominent, for Motion M2, Deltoid muscle group shows maximum activation while for Motion M3, TRILONG shows maximum activation followed by LAT and DEL group. In terms of magnitude of activity, activation of Motion M2 is more with respect to Motion M1. Motion M3 in many ways is a hybrid set of Motion M1 and Motion M2 and this nature is evident in the weight distribution profile.

Muscle activation for all three motion types were reconstructed with synergy equivalent to 85% similarity index (Synergy 8). Individual muscle force, joint torque and energy required were calculated for each of the motion, driven through forward dynamics using reconstructed muscle activation.

TABLE 2 and TABLE 3 show dynamic variables calculated from reconstructed activation with 85% similarity synergy value.

TABLE 2

Dynamic variables (joint loading and muscle force) calculated from reconstructed activation with 85% similarity synergy value.

| Motion | Minimum Synergy | Joint Loading (Nm) | | | | Muscle Force(N) | | |
|---|---|---|---|---|---|---|---|---|
| | | S1 | S2 | S3 | Elbow | Shoulder | Elbow | Forearm |
| M1 | 4 | 2.435 | 1.505 | 1.31 | 1.922 | 110.44 | 87.51 | 57.83 |
| M2 | 5 | 2.237 | 1.426 | 1.129 | 1.768 | 138.07 | 94.37 | 58.29 |
| M3 | 3 | 1.462 | 1.07 | 1.28 | 1.373 | 121.11 | 54.08 | 40.77 |

TABLE 3

Dynamic variables (trajectory error and energy consumption) calculated from reconstructed activation with 85% similarity synergy value.

| Motion | Minimum Synergy | Trajectory error % (elbow) | Muscle energy Consumption (refer equation 5 below) |
|---|---|---|---|
| M1 | 4 | 3.73 | 42.17 |
| M2 | 5 | 4.11 | 47.67 |
| M3 | 3 | 2.92 | 37.84 |

During rehabilitation exercise, the main focus remains on increasing joint range of motion with minimum muscle restraint. In such cases, for any point to point motion, retracing minimum energy path is the most efficient way to complete a task. Present analysis shows that motion M3, which is due to shoulder configuration having a combination of both rotational and elevation component, produces minimum energy to trace a desired trajectory. Gravity and rotation vector component of Motion 3 (M3) is better suited in terms of energy optimization to complete the hand reaching task. In terms of synergy subspace, M3 requires the least synergy (synergy 3) to reach reconstructable activation range. Due to this, error in trajectory regeneration is also less compared to the other two motions. Results indicate a direct relation between the synergy subspace and change in elevation and rotation pattern of shoulder which corresponds to gravity and directional component. Selecting an optimal trajectory in simulation platform may help to evaluate the synergy recruitment and energy cost and can be used to create personalized rehabilitation therapy.

Accordingly, for any rehabilitation exercise involving motion tasks such as say, arm reaching motions, in accordance with the present disclosure, synergistic recruitment approach is used to find the optimized trajectory and the trajectories are ranked accordingly. So for any motion task in a given work-space, an optimal positioning of joint and muscle activation can be ranked and chosen accordingly to get the best possible result with rehabilitation exercise.

Figure 6:
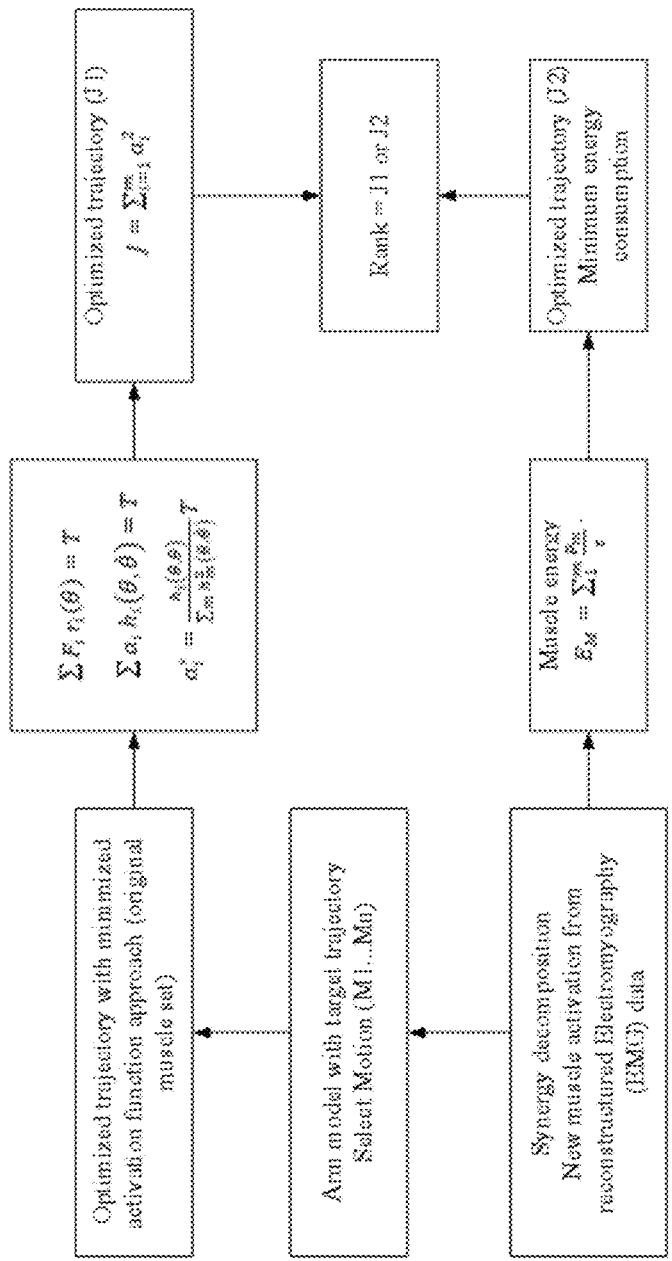
FIG. 6 is an exemplary flow diagram illustrating steps for ranking a trajectory associated with each motion profile and identifying an optimized trajectory in the method of FIG. 4A through FIG. 4E, for selecting a corresponding neuromotor rehabilitation therapy, in accordance with some embodiments of the present disclosure.

In accordance with the present disclosure, if there is limited lesion and muscle activity is in the process of recovering a base threshold (as seen after some period of therapy) a ranking method J1 is applied. And if there is substantial lesion and muscle degeneration such that new muscle synergy for a motion task needs to be programmed, a ranking method J2 is applied to select exercises for rehabilitation, after personalizing the arm model according to subject's condition. FIG. 6 is an exemplary flow diagram illustrating steps for ranking a trajectory associated with each motion profile and identifying an optimized trajectory for selecting a corresponding neuromotor rehabilitation therapy, in accordance with some embodiments of the present disclosure.

Ranking method J1: In an embodiment of the present disclosure, the one or more processors 104, are configured to compute, at step 416, a cost function J representative of muscular effort at each time instant for m number of muscle actuators using the activation value a for each motion profile associated with each of the one or more motion tasks, wherein the cost function is represented as $$J = \Sigma_{i=1}^{m} a_i^2 \quad \rightarrow (6)$$

In an embodiment, the cost function J is subjected to a constraint $$\Sigma F_i r_i(\theta) = T \quad \rightarrow (7)$$

where, F is the muscle force of the arm model and T is a moment balancing torque of the arm in a workspace involving $\tau_m$ and the joint torque using equations (1) and (2). Modifying equation (7) with the equation (1) and the arm model, the constraint may be redefined as $$\Sigma a_i h_i(\theta, \dot{\theta}) = T \quad \rightarrow (8)$$

where, $h_i(\theta, \dot{\theta})$ is a nonlinear transfer function, linking muscle activity to Torque space, similar to Jacobian, accounting for the force-length, force velocity, maximum force, moment arm and pennation angle of any muscle. Solving the optimization problem leads to the solution $$a_i^* = \frac{h_i(\theta, \dot{\theta})}{\sum_m h_m^2(\theta, \dot{\theta})} T \rightarrow \quad (9)$$

The optimized solution leads to selection of m number of muscles that are optimized in muscle force and total torque for a given arm position, defined by joint angles of elbow and shoulder joint.

Accordingly, in an embodiment of the present disclosure, the one or more processors 104, are configured to rank, at step 418, a trajectory associated with each motion profile associated with each of the one or more motion tasks based on the computed cost function J. A motion profile associated with each of the one or more motion tasks having a minimum value for the cost function J is identified as an optimized trajectory at step 420. Finally, a neuromotor rehabilitation therapy corresponding to the identified optimized trajectory for each of the one or more motion tasks is selected from a repository, at step 422, wherein the identified optimized trajectory is indicative of optimal positioning of join and muscle activation.

Ranking method J2: In the J2 ranking method, the reconstructed muscle EMG data, at step 410, is utilized. In an embodiment of the present disclosure, the one or more processors 104, are configured to calculate, at step 424, muscle energy consumption $E_M$ from the muscle force $\tau_m$ and the joint velocity $\dot{q}$ for the corresponding one or more motion tasks associated with the regenerated trajectory. In an embodiment, calculating muscle energy consumption is represented by:

$$E_M = \sum_1^m \frac{P_m}{t} \rightarrow \quad (5)$$

where $P_m$ represents muscle power according to $P_m = \tau_m \cdot \dot{q}$, m represents the number of muscle actuators and M denotes motion.

At step 426, the regenerated trajectory associated with each of the one or more motion tasks is ranked based on the calculated muscle energy consumption of equation (5). The regenerated trajectory associated with each of the one or more motion tasks having a minimum value for the muscle energy consumption $E_M$ is identified as an optimized trajectory, at step 428. Finally, a neuromotor rehabilitation therapy corresponding to the identified optimized trajectory for each of the one or more motion tasks is selected from a repository, at step 430, wherein the identified optimized trajectory is indicative of optimal positioning of joint and muscle activation.

The method and system of the present disclosure thus models the human arm (upper limb) motion dynamics to study synergy variation for different shoulder configuration.

The personalized neuromusculoskeletal model of the arm of the present disclosure with optimized set of muscle actuators allows different motions to be simulated using various possible joint configuration. Three exemplary point to point reaching motion were generated with varying shoulder elevation and rotation, while maintaining fixed elbow trajectory. Muscle activation for the motion were calculated and synergy space was derived for the three-reaching motion. Analysis reveals that both orientation and elevation of shoulder joint dictates muscle recruitment pattern for fixed elbow motion and minimum energy trajectory corresponds to minimum synergy configuration. Synergy space configuration and energy optimized trajectory thus obtained, enables planning a personalized rehabilitation therapy for neuromotor disabilities such as post stroke patients and may also help in better control of neuro-prosthetic arms.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising the steps of:
personalizing, via one or more hardware processors, a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF, wherein the anthropometric measurements of the subject include height, weight, triceps and mid-upper-arm circumference that provides a proxy measure of body composition including muscularity, fat free mass and fat mass, wherein the neuromusculoskeletal arm model captures dynamics of glenohumeral joint for specific point to point hand reaching task involving active elbow flexion, and wherein the one or more motion tasks resemble point to point hand reaching tasks in a three-dimensional plane, keeping trajectory of the elbow joint fixed in all three motions, M1, M2 and M3 and the motions resemble routine exercise motion to regain joint operative range of motion after stroke or any rehabilitation specific to neuro-motor disorder; and
optimizing, via the one or more hardware processors, the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration:

calculating a muscle torque $\tau_m$ indicative of a muscle force based on a moment arm, an activation value a obtained from a muscle Electromyography (EMG) data, a normalized length l and a normalized velocity i̇ of each muscle actuator in the set of muscle actuators, wherein when a muscle is neurally excited, the activation value increases and when the muscle's excitation decreases, the activation value decreases;

calculating a joint torque indicative of loading on each of the three joints, wherein the joint torque is based on an acceleration q̈ due to the joint torque t, the joint angle q, an inertia tensor function Q, a mass matrix M, a Coriolis component C, a gravity component G and an external force F applied to the neuromusculoskeletal arm model;

generating a trajectory associated with a corresponding motion profile for each of the one or more motion tasks based on forward dynamics using the calculated muscle torque and the calculated joint torque; and evaluating a mean square error between the generated trajectory and a target trajectory associated with a corresponding motion profile for each of the one or more motion tasks, until the evaluated mean square error is less than a pre-defined threshold; identifying, via the one or more hardware processors, the set of the muscle actuators with the reduced number of muscle actuators at the end of the iterative steps as the optimized set of muscle actuators to perform the one or more motion tasks; and estimating optimal muscle synergy, via the one or more hardware processors, corresponding to the one or more motion tasks using Non-Negative Matrix Factorization (NNMF), wherein the NNMF reduces a number of commands needed for controlling the optimized set of muscle actuators into a low dimensional subspace, wherein the muscle synergy is used to derive redundant muscle information from the optimized set of muscle actuators, which aids to recreate desired motion if any of the major muscles get damaged due to motor injury, wherein the personalized neuromusculoskeletal arm model with the optimized set of muscle actuators allows different motions to be simulated using various possible joint configuration and both an orientation and an elevation of the shoulder joint dictates muscle recruitment pattern for fixed elbow motion, and a minimum energy trajectory corresponds to a minimum synergy configuration, wherein a similarity index value of 75% for reconstruction of activation, M1 has minimum synergy value of 4, M2 has minimum synergy value of 5 and M3 has minimum synergy value of 3, and M3 corresponding to a configuration due to alteration of both shoulder rotation and elevation shows minimum synergy requirement for reconstruction, wherein a synergy space configuration and an energy optimized trajectory enables planning a personalized rehabilitation therapy for post stroke patients with neuromotor disabilities and aid in control of neuroprosthetic arms.

2. The processor implemented method of claim 1, wherein the step of calculating the muscle torque is represented by the equation $\tau_m = \lfloor R(q) \rfloor f(a,l,\dot{l})$; and the step of calculating the joint torque is represented by the equation $\ddot{q} = [M(Q)]^{-1}\{\tau + C((q,\dot{q}) + G(q) + F)\}$, wherein q̇ represents joint velocity.

3. The processor implemented method of claim 2, further comprising:

reconstructing, via the one or more hardware processors, the muscle EMG data using the estimated optimal muscle synergy to obtain a synergy reconstructed EMG data;

generating, via the one or more hardware processors, an activation map for each of the one or more motion tasks based on the synergy reconstructed EMG data, wherein the activation map is an aggregation of the activation value a of each of the muscle actuators in the optimized set of muscle actuators; and regenerating, via the one or more hardware processors, the trajectory associated with a corresponding motion profile for each of the one or more motion tasks based on the forward dynamics by providing the generated activation map for each of the one or more motion tasks to the personalized musculoskeletal arm model.

4. The processor implemented method of claim 3, wherein the step of estimating an optimal muscle synergy comprises deriving a synergy space for each of the one or more motion profiles by:

computing number of commands needed for controlling the optimized set of muscle actuators based on the NNMF using a matrix Z of the reconstructed EMG data of muscle actuators in the optimized set of muscle actuators, wherein $Z \in X^{m*t}$, 'm' and 't' represent number of muscle actuators and number of time data, respectively such that Z=WC+E, wherein $W \in X^{m*n}$, W defines the synergy space and is a normalized row vector: $|W^i|=1$ and $W^i \in X^m$ and defines a synergy space, n is the number of control commands, n<m, and $C \in X^{n*t}$, C is a column matrix containing n commands to control m muscle actuators in the synergy space, $E \in X^{m*t}$, E is an error between Z and WC; and determining the optimal muscle synergy based on a similarity index $$L = 100\left(1 - \frac{1}{m}\sum_{i=1}^{m} \frac{\sqrt{\frac{1}{t}\sum_{j=1}^{t} E_{ij}^2}}{\sqrt{\frac{1}{t}\sum_{j=1}^{t} Z_{ij}'^2}}\right)$$

where, Z'=WC, and $E_{ij}$ and $Z_{ij}$ are the elements of matrices E and Z, respectively.

5. The processor implemented method of claim 3, further comprising:

calculating, via the one or more hardware processors, muscle energy consumption $E_M$ from the muscle force $\tau_m$ and the joint velocity q̇ for the corresponding one or more motion tasks associated with the regenerated trajectory;

ranking, via the one or more hardware processors, the regenerated trajectory associated with each of the one or more motion tasks based on the calculated muscle energy consumption $E_M$;

identifying, via the one or more hardware processors, the regenerated trajectory associated with each of the one or more motion tasks having a minimum value for the muscle energy consumption $E_M$ as an optimized trajectory; and selecting, via the one or more hardware processors, from a repository, a neuromotor rehabilitation therapy corresponding to the identified optimized trajectory for each of the one or more motion tasks, wherein the identified optimized trajectory is indicative of optimal positioning of joint and muscle activation.

6. The processor implemented method of claim 5, wherein the step of calculating muscle energy consumption is represented by:

$$E_M = \sum_{1}^{m} \frac{P_m}{t}$$

where $P_m$ represents muscle power according to $P_m = \tau_m \cdot \dot{q}$, m represents the number of muscle actuators and M denotes motion.

7. The processor implemented method of claim 1, further comprising:
computing, via the one or more hardware processors, a cost function J representative of muscular effort at each time instant for m number of muscle actuators using the activation value a for each motion profile associated with each of the one or more motion tasks, wherein the cost function is represented as $J = \sum_{i=1}^{m} a_i^2$;
ranking, via the one or more hardware processors, a trajectory associated with each motion profile associated with each of the one or more motion tasks based on the computed cost function J;
identifying, via the one or more hardware processors, a motion profile associated with each of the one or more motion tasks having a minimum value for the cost function J as an optimized trajectory; and
selecting, via the one or more hardware processors, from a repository, a neuromotor rehabilitation therapy corresponding to the identified optimized trajectory for each of the one or more motion tasks, wherein the identified optimized trajectory is indicative of optimal positioning of joint and muscle activation.

8. The processor implemented method of claim 1, wherein a shoulder abduction-adduction values for the three motions are zero, a shoulder flexion-extension values for the three motions are 90 degrees, wherein a shoulder internal-external rotation for the M1 is −45 degree, the M2 is 0 degree, the M3 is 20 degree, and an elbow flexion ranges for M1, M2, M3 are 0-105 degrees.

9. The processor implemented method of claim 1, wherein the optimized set of muscle actuators includes the reduced set of 27 muscle actuators from 49 muscle actuators distributed in three groups of 14 muscle actuators controlling the ball and socket shoulder joint, 9 muscle actuators for the elbow joint and 4 muscle actuators controlling a forearm with a wrist movement, wherein the distribution of the muscle actuators into groups is based on a type of motion task to be performed by the subject, wherein when the activation is decomposed in the synergy space, the activation is represented through individual muscle weights and a neural command, wherein weight distribution shows which muscle have higher response for a particular neural command at a given time and each synergy has a different activation combination across muscles, with some muscle contributing more in terms of activation than others, wherein the weight varies with change in the synergy for same motion.

10. A system (100) comprising:
one or more data storage devices operatively coupled to one or more hardware processors via the one or more input/output interfaces; and configured to store instructions configured for execution via the one or more hardware processors to:
personalize a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF, wherein the anthropometric measurements of the subject include height, weight, triceps and mid-upper-arm circumference that provides a proxy measure of body composition including muscularity, fat free mass and fat mass, wherein the neuromusculoskeletal arm model captures dynamics of glenohumeral joint for specific point to point hand reaching task involving active elbow flexion, and wherein the one or more motion tasks resemble point to point hand reaching tasks in a three-dimensional plane, keeping trajectory of the elbow joint fixed in all three motions, M1, M2 and M3 and the motions resemble routine exercise motion to regain joint operative range of motion after stroke or any rehabilitation specific to neuro-motor disorder;
optimize the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration by:
calculating a muscle torque indicative of a muscle force based on a moment arm, an activation value a obtained from a muscle Electromyography (EMG) data, a normalized length l and a normalized velocity i̇ of each muscle actuator in the set of muscle actuators, wherein when a muscle is neurally excited, the activation value increases and when the muscle's excitation decreases, the activation value decreases;
calculating a joint torque indicative of loading on each of the three joints, wherein the joint torque is based on an acceleration q̈ due to the joint torque τ, the joint angle q, an inertia tensor function Q, a mass matrix M, a Coriolis component C, a gravity component G and an external force F applied to the neuromusculoskeletal arm model;
generating a trajectory associated with a corresponding motion profile for each of the one or more motion tasks based on forward dynamics using the calculated muscle torque and the calculated joint torque; and
evaluating a mean square error between the generated trajectory and a target trajectory associated with a corresponding motion profile for each of the one or more motion tasks;
until the evaluated mean square error is less than a pre-defined threshold;
identify the set of the muscle actuators with the reduced number of muscle actuators at the end of the iterative steps as the optimized set of muscle actuators to perform the one or more motion tasks; and
estimating optimal muscle synergy, via the one or more hardware processors, corresponding to the one or more motion tasks using Non-Negative Matrix Factorization (NNMF), wherein the NNMF reduces a number of commands needed for controlling the optimized set of muscle actuators into a low dimensional subspace, wherein the muscle synergy is used to derive redundant muscle information from the optimized set of muscle actuators, which aids to recreate desired motion if any of the major muscles get damaged due to motor injury, wherein the personalized neuromusculoskeletal arm model with the optimized set of muscle actuators allows different motions to be simulated using various possible joint configuration and both an orientation and an elevation of the shoulder joint dictates muscle recruitment pattern for fixed elbow motion, and a minimum energy trajectory corresponds to a minimum synergy configuration, wherein a similarity index value of 75% for reconstruction of activation, M1 has minimum synergy value of 4, M2 has minimum synergy value of 5 and M3 has minimum synergy value of 3, and M3 corresponding to a configuration due to alteration of both shoulder rotation and elevation shows minimum synergy requirement for reconstruction, wherein a synergy space configuration and an energy optimized trajectory enables planning a personalized rehabilitation therapy for post stroke patients with neuromotor disabilities and aid in control of neuroprosthetic arms.

11. The system of claim 10, wherein the one or more hardware processors are further configured to calculate the muscle torque based on the equation $\tau_m = R(q) f(a,l,\dot{l})$; and further calculate the joint torque represented by the equation $\ddot{q} = [M(Q)]^{-1} \{\tau + C((q,\dot{q}) + G(q) + F)\}$, wherein $\dot{q}$ represents joint velocity.

12. The system of claim 11, wherein the one or more hardware processors are further configured to:
reconstruct the muscle EMG data using the estimated optimal muscle synergy to obtain a synergy reconstructed EMG data;
generate an activation map for each of the one or more motion tasks based on the synergy reconstructed EMG data, wherein the activation map is an aggregation of the activation value a of each of the muscle actuators in the optimized set of muscle actuators; and
regenerate the trajectory associated with a corresponding motion profile for each of the one or more motion tasks based on the forward dynamics by providing the generated activation map for each of the one or more motion tasks to the personalized musculoskeletal arm model.

13. The system of claim 12, wherein the one or more hardware processors are configured to estimate an optimal muscle synergy by deriving a synergy space for each of the one or more motion profiles by performing:
computing number of commands needed for controlling the optimized set of muscle actuators based on the NNMF using a matrix Z of the reconstructed EMG data of muscle actuators in the optimized set of muscle actuators, wherein $Z \in X^{m*t}$, 'm' and 't' represent number of muscle actuators and number of time data, respectively such that $Z = WC + E$, wherein
$W \in X^{m*n}$, W defines the synergy space and is a normalized row vector: $|W^i| = 1$ and $W^i \in X^m$ and defines a synergy space, n is the number of control commands, n<m, and $C \in X^{n*t}$, C is a column matrix containing n commands to control m muscle actuators in the synergy space, $E \in X^{m*t}$, E is an error between Z and WC; and
determining the optimal muscle synergy based on a similarity index $$L = 100\left(1 - \frac{1}{m}\sum_{i=1}^{m} \frac{\sqrt{\frac{1}{t}\sum_{j=1}^{t} E_{ij}^2}}{\sqrt{\frac{1}{t}\sum_{j=1}^{t} Z_{ij}'^2}}\right)$$

where, $Z' = WC$, and $E_{ij}$ and $Z_{ij}$ are the elements of matrices E and Z, respectively.

14. The system of claim 12, wherein the one or more hardware processors are further configured to:
calculate muscle energy consumption $E_M$ from the muscle force $\tau_m$ and the joint velocity $\dot{q}$ for the corresponding one or more motion tasks associated with the regenerated trajectory;
rank, the regenerated trajectory associated with each of the one or more motion tasks based on the calculated muscle energy consumption $E_M$;
identify the regenerated trajectory associated with each of the one or more motion tasks having a minimum value for the muscle energy consumption $E_M$ as an optimized trajectory; and
select from a repository, a neuromotor rehabilitation therapy corresponding to the identified optimized trajectory for each of the one or more motion tasks, wherein the identified optimized trajectory is indicative of optimal positioning of joint and muscle activation.

15. The system of claim 14, wherein the one or more hardware processors are configured to calculate muscle energy consumption based on the equation:

$$E_M = \sum_{1}^{m} \frac{P_m}{t}$$

where $P_m$ represents muscle power according to $P_m = \tau_m \cdot \dot{q}$, $\tau_m$ represents the muscle force, q represents the velocity, m represents the number of muscle actuators and M denotes motion.

16. The system of claim 10, wherein the one or more hardware processors are further configured to:
compute a cost function J representative of muscular effort at each time instant for m number of muscle actuators using the activation value a for each motion profile associated with each of the one or more motion tasks, wherein the cost function is represented as $J = \sum_{i=1}^{m} a_i^2$;
rank a trajectory associated with each motion profile associated with each of the one or more motion tasks based on the computed cost function J;
identify a motion profile associated with each of the one or more motion tasks having a minimum value for the cost function J as an optimized trajectory; and
select from a repository, a neuromotor rehabilitation therapy corresponding to the identified optimized trajectory for each of the one or more motion tasks, wherein the identified optimized trajectory is indicative of optimal positioning of joint and muscle activation.

17. A computer program product comprising a non-transitory computer readable medium having a computer readable program embodied therein, wherein the computer readable program, when executed on a computing device, causes the computing device to:

personalize a neuromusculoskeletal arm model having three joints and a set of muscle actuators, wherein the neuromusculoskeletal arm model is adapted to conform with anthropometric measurements of a subject and is configured to perform one or more motion tasks by the subject using the three joints being a ball and socket shoulder joint along with clavicle and scapula having three degrees of freedom (DoF), an elbow joint with one DoF and a wrist joint having three DoF, wherein the anthropometric measurements of the subject include height, weight, triceps and mid-upper-arm circumference that provides a proxy measure of body composition including muscularity, fat free mass and fat mass, wherein the neuromusculoskeletal arm model captures dynamics of glenohumeral joint for specific point to point hand reaching task involving active elbow flexion, and wherein the one or more motion tasks resemble point to point hand reaching tasks in a three-dimensional plane, keeping trajectory of the elbow joint fixed in all three motions, M1, M2 and M3 and the motions resemble routine exercise motion to regain joint operative range of motion after stroke or any rehabilitation specific to neuro-motor disorder;

optimize the set of muscle actuators by performing the following iterative steps starting with the set of muscle actuators in the personalized neuromusculoskeletal arm model in a first iteration and every subsequent iteration having a reduced number of muscle actuators in the set of muscle actuators compared to a previous iteration by:

calculating a muscle torque indicative of a muscle force based on a moment arm, an activation value a obtained from a muscle Electromyography (EMG) data, a normalized length l and a normalized velocity $\dot{l}$ of each muscle actuator in the set of muscle actuators, wherein when a muscle is neurally excited, the activation value increases and when the muscle's excitation decreases, the activation value decreases;

calculating a joint torque indicative of loading on each of the three joints, wherein the joint torque is based on an acceleration $\ddot{q}$ due to the joint torque t, the joint angle q, an inertia tensor function Q, a mass matrix M, a Coriolis component C, a gravity component G and an external force F applied to the neuromusculoskeletal arm model;

generating a trajectory associated with a corresponding motion profile for each of the one or more motion tasks based on forward dynamics using the calculated muscle torque and the calculated joint torque; and evaluating a mean square error between the generated trajectory and a target trajectory associated with a corresponding motion profile for each of the one or more motion tasks;

until the evaluated mean square error is less than a pre-defined threshold;

identify the set of the muscle actuators with the reduced number of muscle actuators at the end of the iterative steps as the optimized set of muscle actuators to perform the one or more motion tasks; and estimating optimal muscle synergy, via the one or more hardware processors, corresponding to the one or more motion tasks using Non-Negative Matrix Factorization (NNMF), wherein the NNMF reduces a number of commands needed for controlling the optimized set of muscle actuators into a low dimensional subspace, wherein the muscle synergy is used to derive redundant muscle information from the optimized set of muscle actuators, which aids to recreate desired motion if any of the major muscles get damaged due to motor injury, wherein the personalized neuromusculoskeletal arm model with the optimized set of muscle actuators allows different motions to be simulated using various possible joint configuration and both an orientation and an elevation of the shoulder joint dictates muscle recruitment pattern for fixed elbow motion, and a minimum energy trajectory corresponds to a minimum synergy configuration, wherein a similarity index value of 75% for reconstruction of activation, M1 has minimum synergy value of 4, M2 has minimum synergy value of 5 and M3 has minimum synergy value of 3, and M3 corresponding to a configuration due to alteration of both shoulder rotation and elevation shows minimum synergy requirement for reconstruction, wherein a synergy space configuration and an energy optimized trajectory enables planning a personalized rehabilitation therapy for post stroke patients with neuromotor disabilities and aid in control of neuro-prosthetic arms.

18. The computer program product of claim 17, wherein the computer readable program further causes the computing device to:

reconstruct the muscle EMG data using the estimated optimal muscle synergy to obtain a synergy reconstructed EMG data;

generate an activation map for each of the one or more motion tasks based on the synergy reconstructed EMG data, wherein the activation map is an aggregation of the activation value a of each of the muscle actuators in the optimized set of muscle actuators; and regenerate the trajectory associated with a corresponding motion profile for each of the one or more motion tasks based on the forward dynamics by providing the generated activation map for each of the one or more motion tasks to the personalized musculoskeletal arm model.

19. The computer program product of claim 18, wherein the computer readable program further causes the computing device to:

calculate muscle energy consumption $E_M$ from the muscle force $\tau_m$ and the joint velocity $\dot{q}$ for the corresponding one or more motion tasks associated with the regenerated trajectory;

rank, the regenerated trajectory associated with each of the one or more motion tasks based on the calculated muscle energy consumption $E_M$;

identify the regenerated trajectory associated with each of the one or more motion tasks having a minimum value for the muscle energy consumption $E_M$ as an optimized trajectory; and select from a repository, a neuromotor rehabilitation therapy corresponding to the identified optimized trajectory for each of the one or more motion tasks, wherein the identified optimized trajectory is indicative of optimal positioning of joint and muscle activation.

20. The computer program product of claim 17, wherein the computer readable program further causes the computing device to:

compute a cost function J representative of muscular effort at each time instant for m number of muscle actuators using the activation value a for each motion profile associated with each of the one or more motion tasks, wherein the cost function is represented as $J=\Sigma_{i=1}^{m} a_i^2$;

rank a trajectory associated with each motion profile associated with each of the one or more motion tasks based on the computed cost function J;

identify a motion profile associated with each of the one or more motion tasks having a minimum value for the cost function J as an optimized trajectory; and select from a repository, a neuromotor rehabilitation therapy corresponding to the identified optimized trajectory for each of the one or more motion tasks, wherein the identified optimized trajectory is indicative of optimal positioning of joint and muscle activation.

\* \* \* \* \*